(12) United States Patent
Shewmake et al.

(10) Patent No.: US 7,416,895 B2
(45) Date of Patent: Aug. 26, 2008

(54) METHOD FOR IDENTIFYING AT RISK CARDIOVASCULAR DISEASE PATIENTS

(75) Inventors: David Shewmake, San Francisco, CA (US); Frank Ruderman, San Carlos, CA (US); Christopher Boggess, San Francisco, CA (US); Faith Clendenen, Oakland, CA (US)

(73) Assignee: Berkeley Heartlab, Inc., Burlingame, CA (US)

( * ) Notice: Subject to any disclaimer, the term of this patent is extended or adjusted under 35 U.S.C. 154(b) by 105 days.

(21) Appl. No.: 10/412,838

(22) Filed: Apr. 12, 2003

(65) Prior Publication Data

US 2003/0235918 A1 Dec. 25, 2003

Related U.S. Application Data

(60) Provisional application No. 60/390,796, filed on Jun. 21, 2002.

(51) Int. Cl.
*G01N 33/92* (2006.01)

(52) U.S. Cl. ............... 436/71; 436/63; 436/13

(58) Field of Classification Search .......... 436/63, 436/71, 173, 13; 204/450, 456; 705/2; 435/2
See application file for complete search history.

(56) References Cited

U.S. PATENT DOCUMENTS

| | | | | | |
|---|---|---|---|---|---|
| 5,589,104 | A | * | 12/1996 | Bambeck | .............. 516/103 |
| 5,925,229 | A | * | 7/1999 | Krauss et al. | ........... 204/608 |
| 6,576,471 | B2 | * | 6/2003 | Otvos | .................. 436/71 |
| 6,812,033 | B2 | * | 11/2004 | Shewmake et al. | ......... 436/71 |
| 2003/0136680 | A1 | * | 7/2003 | Benner et al. | .......... 204/549 |
| 2003/0208108 | A1 | * | 11/2003 | Shewmake et al. | ..... 600/300 |

FOREIGN PATENT DOCUMENTS

WO 01/41037 * 6/2001

OTHER PUBLICATIONS

Superko. "Lipoprotein Subclasses and Atherosclerosis". Frontiers in Bioscience, vol. 6, Mar. 1, 2001, pp. 355-365.*

* cited by examiner

*Primary Examiner*—Maureen M Wallenhorst
(74) *Attorney, Agent, or Firm*—McDonnell Boehnen Hulbert & Berghoff LLP

(57) ABSTRACT

This invention is directed to a data base which contains data for HDL2b, LDL IIIa & LDL IIIb and LDL IVb subclasses all in mg/Dl and which is correlated to cardiovascular disease.

1 Claim, 24 Drawing Sheets

| | Case | TG | TC | HDLC | LDLC | Chem Values apoAI | apoB | Lp(a) | LDL Pheno | LDL Pk 1 | LDL Pk 2 | 9-8 | 8-7 | 7-6 | 6.0-5.5 | 5.5-5.0 | 5.0-4.5 |
|---|---|---|---|---|---|---|---|---|---|---|---|---|---|---|---|---|---|
| 1 | 14917 | 216 | 217 | 56 | 118 | | | 41.6 | A | 267.5 | | 0.4 | 1.9 | 5.1 | 5.4 | 7.8 | 10.5 |
| 2 | 14922 | 52 | 176 | 63 | 103 | 128 | 75 | 9.6 | A | 263.5 | | 0.4 | 2.8 | 10.8 | 11.2 | 14.2 | 16.0 |
| 3 | 14923 | 53 | 157 | 51 | 95 | 99 | 72 | 8.4 | A | 264.1 | | 0.1 | 1.5 | 6.8 | 7.7 | 9.7 | 11.0 |
| 4 | 14927 | 230 | 225 | 56 | 123 | 150 | 116 | 0.4 | A | 264.4 | | 0.6 | 4.8 | 17.6 | 17.7 | 20.6 | 19.8 |
| 5 | 14929 | 227 | 247 | 62 | 140 | 167 | 127 | 0.1 | B | 254.7 | | 0.0 | 1.9 | 11.3 | 12.9 | 17.1 | 18.4 |
| 6 | 14948 | 197 | 218 | 31 | 148 | 90 | 126 | 42.0 | B | 252.3 | 264.5 | 0.5 | 3.5 | 11.6 | 0.0 | 0.1 | 0.7 |
| 7 | 14949 | 77 | 137 | 49 | 73 | 106 | 62 | 8.4 | A | 269.5 | | 0.0 | 0.0 | 0.0 | 11.9 | 14.4 | 14.9 |
| 8 | 14962 | 124 | 153 | 38 | 90 | 100 | 87 | 16.2 | B | 246.6 | 258.8 | 0.0 | 0.0 | 0.2 | 1.2 | 2.4 | 3.6 |
| 9 | 14963 | 66 | 176 | 45 | 118 | 100 | 86 | 3.3 | B | 257.2 | 262.6 | 0.0 | 0.0 | 0.0 | 0.2 | 0.9 | 2.1 |
| 10 | 14964 | 103 | 169 | 58 | 90 | 122 | 82 | 65.5 | A | 268.2 | | 0.0 | 1.1 | 7.2 | 9.8 | 14.4 | 17.8 |
| 11 | 14983 | 109 | 216 | 83 | 111 | 178 | 87 | 27.2 | A | 269.2 | | 1.5 | 9.4 | 31.7 | 29.4 | 33.0 | 31.1 |
| 12 | 14984 | 106 | 176 | 43 | 112 | 103 | 90 | 4.1 | B | 265.5 | | 0.0 | 0.2 | 1.7 | 2.4 | 4.0 | 6.0 |
| 13 | 14995 | 234 | 233 | 37 | 149 | 104 | 132 | 11.0 | B | 249.3 | | 0.0 | 0.0 | 0.0 | 0.2 | 1.2 | 2.7 |
| 14 | 15047 | 104 | 243 | 36 | 186 | 97 | 122 | 12.5 | B | 252.5 | 262.0 | 0.0 | 0.0 | 0.0 | 0.0 | 0.0 | 0.5 |
| 15 | 15051 | 90 | 157 | 41 | 98 | 107 | 83 | 2.5 | B | 264.7 | 255.1 | 0.0 | 0.1 | 1.1 | 2.2 | 3.8 | 6.0 |
| 16 | 15058 | 88 | 194 | 35 | 141 | 86 | 101 | 15.3 | A | 267.2 | 256.9 | 0.0 | 0.0 | 0.0 | 0.0 | 0.0 | 0.0 |
| 17 | 15059 | 178 | 159 | 23 | 100 | 73 | 106 | 1.4 | B | 245.6 | | 0.0 | 0.0 | 0.0 | 0.0 | 0.1 | 0.7 |
| 18 | 15077 | 33 | 184 | 71 | 106 | | | 2.2 | A | 277.2 | | 0.6 | 5.9 | 20.2 | 19.3 | 22.8 | 24.2 |
| 19 | 15078 | 50 | 181 | 75 | 96 | | | 8.9 | A | 269.0 | 276.7 | 1.9 | 8.4 | 23.2 | 20.6 | 23.0 | 23.4 |
| 20 | 15081 | 162 | 228 | 77 | 119 | 180 | 90 | 27.3 | A | 269.0 | | 1.3 | 9.2 | 29.6 | 24.5 | 26.7 | 26.6 |
| 21 | 15082 | 143 | 186 | 44 | 113 | 137 | 69 | 4.1 | — | 261.6 | 277.2 | 0.0 | 0.2 | 0.0 | 0.1 | 0.6 | 2.1 |
| 22 | 15094 | 118 | 196 | 46 | 126 | 121 | 92 | 64.6 | B | 254.3 | | 0.0 | 2.0 | 8.1 | 0.7 | 1.6 | 3.0 |
| 23 | 15095 | 177 | 168 | 45 | 88 | 118 | 81 | 59.5 | B | 255.3 | | 0.3 | 0.0 | 0.0 | 9.0 | 12.2 | 15.1 |
| 24 | 15098 | 444 | 181 | 28 | 94 | 107 | 63 | 22.6 | B | 241.6 | | 0.0 | 0.0 | 0.0 | 0.0 | 0.1 | 0.5 |
| 25 | 15105 | 137 | 165 | 56 | 82 | 127 | 73 | 60.8 | B | 267.3 | | 0.2 | 1.9 | 7.2 | 9.1 | 13.1 | 15.6 |
| 26 | 15108 | 311 | 247 | 43 | 142 | 117 | 127 | 4.9 | B | 251.8 | | 0.0 | 0.0 | 0.0 | 0.0 | 0.3 | 1.4 |
| 27 | 15110 | 162 | 214 | 39 | 143 | 101 | 104 | 9.8 | B | 252.7 | | 0.0 | 0.0 | 0.0 | 0.0 | 0.1 | 1.5 |
| 28 | 15113 | 128 | 168 | 37 | 105 | 95 | 83 | 1.6 | A | 264.1 | 256.2 | 0.0 | 0.2 | 1.4 | 2.4 | 0.1 | 1.2 |
| 29 | 15121 | 247 | 333 | 47 | 237 | 143 | 170 | 0.2 | A | 263.5 | | 0.0 | 0.0 | 0.0 | 0.2 | 4.3 | 6.7 |
| 30 | 15124 | 410 | 217 | 44 | 112 | 115 | | 8.5 | B | 249.8 | | 0.0 | 0.0 | 0.0 | 0.0 | 1.1 | 3.0 |
| 31 | 15131 | 108 | 180 | 35 | 123 | 87 | 83 | 11.0 | A | 268.1 | | 0.0 | 0.2 | 0.0 | 0.0 | 0.0 | 0.1 |
| 32 | 15153 | 130 | 192 | 46 | 120 | 124 | 91 | 2.4 | A | 254.7 | | 0.0 | 1.9 | 7.2 | 0.2 | 1.0 | 2.7 |
| 33 | 15156 | 289 | 227 | 35 | 134 | 100 | 124 | 3.5 | B | 252.1 | | 0.2 | 0.0 | 0.0 | 0.0 | 0.0 | 0.4 |
| 34 | 15180 | 119 | 230 | 54 | 152 | 118 | 100 | 3.5 | B | 253.1 | | 0.0 | 0.6 | 5.4 | 7.9 | 11.0 | 13.6 |
| 35 | 15191 | 264 | 232 | 60 | 119 | 156 | 110 | 33.1 | B | 256.4 | 265.0 | 0.7 | 4.0 | 11.2 | 9.7 | 11.4 | 13.2 |
| 36 | 17297 | 364 | 135 | 30 | 32 | 102 | 83 | 2.1 | A | 240.4 | | 0.0 | 0.0 | 0.0 | 0.0 | 0.4 | 1.6 |
| 37 | 17371 | 219 | 238 | 34.5 | 160 | 92 | 119 | 24.8 | A | 264.7 | | 0.0 | 0.0 | 0.0 | 0.0 | 0.0 | 0.3 |

LF Sar LF-T LF-TC LF-HDLC LF-LDLC LF-apoAI LF-apoB LF-Lp(a)

FIGURE 1

| ANUC HDL Fractions | | | | | | | | | | ANUC Total | | Pk F(corr) | 400-350 | 350-300 | 300-250 | 250-200 | 200-150 |
|---|---|---|---|---|---|---|---|---|---|---|---|---|---|---|---|---|---|
| 4.5-4.0 | 4.0-3.5 | 3.5-3.0 | 3.0-2.5 | 2.5-2.0 | 2.0-1.5 | 1.5-1.0 | 1.0-0.5 | 0.5-0.0 | 9-0 | | | | | | | | |
| 14.3 | 20.9 | 31.1 | 43.5 | 53.0 | 52.6 | 43.2 | 27.0 | 3.3 | 319.9 | | 2.0 | 0.0 | 0.0 | 0.0 | 0.9 | 4.7 | 13.8 |
| 18.0 | 21.0 | 26.2 | 33.7 | 39.8 | 39.3 | 30.9 | 16.8 | 0.1 | 281.1 | | 1.9 | 0.0 | 0.0 | 0.0 | 0.0 | 0.0 | 0.0 |
| 12.6 | 15.9 | 22.2 | 29.5 | 35.4 | 34.4 | 29.4 | 18.6 | 2.2 | 236.8 | | 2.2 | 0.0 | 0.0 | 0.0 | 0.3 | 2.4 | 6.7 |
| 19.3 | 22.8 | 30.5 | 38.4 | 41.4 | 36.0 | 25.7 | 7.1 | 0.1 | 302.3 | | 2.3 | 0.0 | 0.0 | 0.1 | 0.8 | 3.0 | 9.3 |
| 19.6 | 25.2 | 36.8 | 50.3 | 58.1 | 53.2 | 39.3 | 18.6 | 0.6 | 363.4 | | 2.2 | 0.0 | 0.0 | 0.1 | 1.6 | 6.6 | 15.6 |
| 2.4 | 5.5 | 12.5 | 23.6 | 34.6 | 41.2 | 37.0 | 22.5 | 0.4 | 180.5 | | 1.8 | 0.0 | 0.0 | 0.0 | 0.0 | 1.4 | 7.1 |
| 14.7 | 15.8 | 20.5 | 28.3 | 33.3 | 31.8 | 25.7 | 13.0 | 0.1 | 239.9 | | 2.2 | 0.0 | 0.0 | 0.0 | 0.0 | 0.0 | 0.0 |
| 5.7 | 9.8 | 17.6 | 28.6 | 38.7 | 41.1 | 34.3 | 19.6 | 0.7 | 203.7 | | 1.9 | 0.0 | 0.0 | 0.0 | 0.5 | 2.8 | 7.4 |
| 4.8 | 10.6 | 20.9 | 34.2 | 45.3 | 46.2 | 35.0 | 13.6 | 0.3 | 214.0 | | 1.9 | 0.0 | 0.0 | 0.0 | 0.0 | 0.0 | 0.0 |
| 20.9 | 25.9 | 33.2 | 40.9 | 45.0 | 41.0 | 30.4 | 12.2 | 0.1 | 299.9 | | 2.3 | 0.0 | 0.0 | 0.0 | 0.0 | 2.3 | 7.3 |
| 30.6 | 36.2 | 47.5 | 57.2 | 58.2 | 45.2 | 29.0 | 8.3 | 0.3 | 448.7 | | 2.3 | 0.0 | 0.0 | 0.0 | 0.0 | 0.1 | 1.3 |
| 9.0 | 14.7 | 25.2 | 37.9 | 48.5 | 48.1 | 36.8 | 16.5 | 0.6 | 251.3 | | 2.1 | 0.0 | 0.0 | 0.0 | 0.0 | 0.8 | 4.7 |
| 4.6 | 10.0 | 21.0 | 34.3 | 44.1 | 44.8 | 33.5 | 9.7 | 0.0 | 206.0 | | 2.0 | 0.0 | 0.2 | 1.3 | 3.6 | 7.9 | 18.8 |
| 2.5 | 6.3 | 14.1 | 27.1 | 40.1 | 47.0 | 40.7 | 25.3 | 3.0 | 206.7 | | 1.8 | 0.0 | 0.0 | 0.0 | 0.0 | 0.6 | 3.4 |
| 9.4 | 16.0 | 26.6 | 38.4 | 45.8 | 43.7 | 35.2 | 14.7 | 0.1 | 243.0 | | 2.2 | 0.0 | 0.0 | 0.0 | 0.0 | 0.0 | 2.0 |
| 0.4 | 1.8 | 6.6 | 16.3 | 28.1 | 37.0 | 33.7 | 20.8 | 2.4 | 147.2 | | 1.7 | 0.0 | 0.0 | 0.0 | 0.0 | 0.0 | 0.8 |
| 2.2 | 4.8 | 9.6 | 16.3 | 23.0 | 27.3 | 19.4 | 3.9 | 0.1 | 107.3 | | 2.6 | 0.0 | 0.0 | 0.0 | 0.0 | 1.6 | 10.2 |
| 25.3 | 27.9 | 32.5 | 36.8 | 35.3 | 29.0 | 19.3 | 5.6 | 0.1 | 304.9 | | 2.7 | 0.0 | 0.0 | 0.0 | 0.0 | 0.0 | 0.0 |
| 23.8 | 25.9 | 30.9 | 35.5 | 33.8 | 28.7 | 19.3 | 5.2 | 0.1 | 303.7 | | 2.5 | 0.0 | 0.0 | 0.0 | 0.0 | 0.0 | 0.0 |
| 29.8 | 41.7 | 55.4 | 63.2 | 60.9 | 49.0 | 30.0 | 6.9 | 0.1 | 454.7 | | 1.7 | 0.0 | 0.0 | 0.0 | 0.4 | 2.5 | 10.0 |
| 4.3 | 8.6 | 17.6 | 34.5 | 51.4 | 59.2 | 48.0 | 27.3 | 2.2 | 255.8 | | 2.0 | 0.0 | 0.0 | 0.0 | 0.7 | 2.8 | 7.7 |
| 5.9 | 11.3 | 21.5 | 35.7 | 48.4 | 51.8 | 40.0 | 19.8 | 0.4 | 240.3 | | 1.9 | 0.0 | 0.0 | 0.5 | 0.3 | 1.8 | 6.6 |
| 17.4 | 22.4 | 32.7 | 45.0 | 51.6 | 48.6 | 35.1 | 12.9 | 0.1 | 312.6 | | 2.2 | 0.0 | 0.0 | 0.0 | 0.0 | 6.1 | 15.1 |
| 1.9 | 4.1 | 10.0 | 20.5 | 32.8 | 41.7 | 36.7 | 20.3 | 0.6 | 169.3 | | 1.9 | 0.0 | 0.2 | 2.5 | 10.8 | 23.3 | 46.2 |
| 17.2 | 19.8 | 25.5 | 33.2 | 39.1 | 37.9 | 30.7 | 15.1 | 0.3 | 266.0 | | 2.0 | 0.0 | 0.0 | 0.0 | 0.3 | 2.2 | 7.3 |
| 4.1 | 11.1 | 23.8 | 40.0 | 53.1 | 54.2 | 43.3 | 20.6 | 0.4 | 261.7 | | 1.9 | 0.0 | 0.2 | 0.8 | 4.2 | 10.4 | 28.1 |
| 3.6 | 7.1 | 13.3 | 22.0 | 31.0 | 36.4 | 31.4 | 18.6 | 1.0 | 160.6 | | 2.0 | 0.0 | 0.0 | 0.0 | 0.6 | 2.9 | 7.2 |
| 4.3 | 11.3 | 23.4 | 37.9 | 48.4 | 47.6 | 37.5 | 20.0 | 1.4 | 252.3 | | 2.2 | 0.2 | 0.2 | 2.5 | 10.8 | 23.3 | 46.2 |
| 10.6 | 19.4 | 33.0 | 47.5 | 58.6 | 60.9 | 51.2 | 24.3 | 0.3 | 166.2 | | 1.9 | 0.0 | 0.3 | 0.0 | 0.5 | 3.1 | 10.8 |
| 6.0 | 11.9 | 23.1 | 39.5 | 53.5 | 55.0 | 43.2 | 24.0 | 1.4 | 233.0 | | 2.0 | 0.0 | 0.0 | 0.0 | 0.0 | 0.2 | 2.2 |
| 1.5 | 4.8 | 12.2 | 24.1 | 35.8 | 37.8 | 30.1 | 13.8 | 0.5 | 320.7 | | 2.0 | 0.0 | 0.3 | 0.7 | 4.2 | 5.9 | 13.4 |
| 5.9 | 11.6 | 20.4 | 30.3 | 36.8 | 33.9 | 23.9 | 4.4 | 0.0 | 171.1 | | 2.2 | 0.0 | 0.0 | 0.8 | 0.6 | 10.4 | 28.1 |
| 1.4 | 4.8 | 11.5 | 21.1 | 30.5 | 34.3 | 30.3 | 14.6 | 0.5 | 149.5 | | 1.9 | 0.0 | 0.0 | 0.0 | 0.0 | 1.0 | 4.6 |
| 15.7 | 19.4 | 27.4 | 38.5 | 47.0 | 43.2 | 32.8 | 16.7 | 0.1 | 279.3 | | 2.2 | 0.0 | 0.3 | 2.1 | 6.9 | 13.1 | 22.5 |
| 15.6 | 21.5 | 33.6 | 49.8 | 62.2 | 62.0 | 50.3 | 26.8 | 1.9 | 373.9 | | 2.1 | 0.0 | 0.0 | 0.0 | 0.5 | 2.7 | 8.0 |
| 3.4 | 7.5 | 16.6 | 28.6 | 38.7 | 38.9 | 30.6 | 13.8 | 0.3 | 180.4 | | 2.1 | 0.0 | 0.0 | 0.0 | 0.5 | 3.1 | 12.1 |
| 1.4 | 4.4 | 12.6 | 24.4 | 35.3 | 38.1 | 29.5 | 14.3 | 1.2 | 161.6 | | 1.9 | 0.0 | 0.2 | 0.0 | 1.8 | 5.9 | 16.0 |

FIGURE 2

| | | | | | | | ANUC LDL Fractions | | | | | | | | | | | | | | | | |
|---|---|---|---|---|---|---|---|---|---|---|---|---|---|---|---|---|---|---|---|---|---|---|---|
|150-100|100-90|90-80|80-70|70-60|60-50|50-40|40-30|30-20|20-18|18-16|16-14|14-12|12-10|10-9|9-8|8-7|7-6|6-5|5-4|4-3|3-2|
|29.6|9.3|10.9|12.9|15.4|16.2|14.0|10.8|8.7|2.8|4.4|6.2|9.3|15.1|11.9|18.7|39.7|65.5|61.8|40.8|17.8|5.2|
|0.0|0.0|0.0|0.0|0.0|0.3|0.9|2.4|4.1|0.0|0.0|0.2|1.6|9.9|19.4|32.1|40.2|42.9|36.6|26.6|17.7|11.3|
|11.6|1.7|2.1|2.6|3.0|3.3|4.4|7.6|11.7|1.4|1.9|2.9|4.2|7.5|8.5|18.3|37.0|51.3|45.5|29.8|18.7|14.9|
|18.1|5.6|6.2|7.3|9.4|12.3|16.5|22.8|30.4|8.2|10.1|11.8|14.7|26.1|24.8|41.3|59.6|56.9|39.4|18.9|6.5|2.6|
|33.5|9.4|10.5|11.1|11.6|12.0|12.8|15.0|21.5|7.8|11.6|14.9|17.8|26.1|19.7|28.2|46.9|71.8|80.2|64.8|30.9|8.9|
|15.0|6.5|8.8|11.7|14.6|17.7|17.7|20.9|25.9|8.0|10.3|13.0|15.5|20.2|14.7|22.4|38.6|56.8|70.7|57.2|30.0|8.8|
|14.4|4.7|5.6|6.5|7.6|0.5|1.5|3.8|7.8|0.0|0.2|1.3|4.4|11.5|14.8|27.1|37.7|35.7|25.6|14.5|6.4|2.2|
|0.0|0.0|0.0|0.0|0.1|9.0|10.9|14.5|19.3|3.0|3.4|4.9|7.7|11.2|7.8|11.0|17.4|26.3|36.0|40.5|32.9|19.6|
|13.9|4.1|5.2|5.9|6.5|7.3|3.0|6.2|14.6|6.7|10.1|14.0|18.4|26.1|19.2|23.6|29.9|41.2|46.8|36.5|16.8|6.2|
|5.6|1.2|1.5|1.8|2.5|6.5|8.3|10.5|13.5|2.7|3.3|4.4|5.9|9.4|11.8|21.3|31.3|34.1|28.6|19.6|13.7|12.3|
|12.1|5.3|6.4|7.5|8.5|3.7|5.4|8.0|15.0|5.0|7.3|10.2|14.5|24.8|25.9|39.5|46.5|37.8|22.2|9.8|4.5|2.5|
|32.0|10.8|12.5|14.4|16.7|9.6|10.9|13.9|18.1|5.8|7.7|9.9|14.2|25.3|21.6|36.4|62.9|69.1|53.0|28.4|10.3|4.5|
|8.3|3.0|3.4|3.8|4.5|19.1|22.8|30.7|42.6|12.7|14.3|16.2|18.9|23.8|15.2|18.6|23.9|40.2|79.2|80.8|51.4|15.6|
|6.0|2.4|3.4|4.7|6.1|5.4|7.1|10.7|16.7|7.5|11.1|15.1|20.7|34.6|26.3|31.6|38.6|54.4|73.8|74.6|45.6|15.0|
|5.5|2.0|3.0|4.0|5.2|7.7|10.1|15.1|21.0|4.3|4.8|6.7|9.3|13.6|10.2|18.1|32.4|45.2|42.8|29.9|17.6|10.6|
|24.9|9.5|11.9|14.2|16.2|6.8|9.1|13.0|19.2|4.5|5.7|10.6|11.1|17.9|14.3|21.5|38.6|60.5|64.7|50.3|27.0|9.5|
|0.0|0.0|0.0|0.0|0.0|17.9|19.8|24.8|32.9|8.4|9.5|1.1|13.7|18.5|11.8|14.0|17.2|22.7|32.9|43.8|41.9|26.9|
|0.0|0.0|0.0|0.0|0.5|0.0|0.0|0.0|0.0|0.0|0.1|3.0|4.6|18.3|34.0|51.6|49.0|40.2|30.5|20.5|12.6|7.9|
|18.7|6.7|7.7|8.8|9.9|0.2|1.2|1.8|5.8|1.9|2.3|9.8|6.5|16.3|19.1|34.5|49.9|46.0|31.5|16.6|7.9|4.4|
|16.2|5.5|6.7|8.4|12.1|11.1|12.8|17.8|22.5|5.1|6.9|18.4|13.1|27.5|32.9|49.4|57.2|43.0|22.0|7.9|3.4|2.8|
|14.5|4.7|5.1|5.9|6.9|17.6|25.9|40.5|62.1|16.1|17.0|11.1|20.4|22.8|12.6|13.5|14.3|14.3|13.1|11.3|9.1|6.4|
|24.8|6.1|6.8|7.6|8.5|8.1|10.5|15.5|22.8|6.5|8.2|8.5|15.7|22.5|16.1|22.1|35.8|54.6|59.9|45.7|23.1|11.3|
|97.9|26.2|29.9|33.0|33.2|9.3|10.6|14.5|20.0|4.9|6.6|5.4|10.5|14.5|11.0|17.0|27.0|38.4|40.0|28.1|12.1|6.0|
|15.6|6.1|7.5|8.8|10.1|29.1|24.4|18.6|18.1|2.7|3.7|5.5|7.4|10.3|6.9|9.1|12.3|18.2|33.3|52.7|51.5|23.9|
|97.9|26.2|29.9|33.0|33.2|10.9|11.5|12.9|14.8|2.9|4.1|5.4|7.4|12.2|12.5|22.1|32.5|34.9|28.8|19.7|12.6|10.6|
|22.9|7.8|9.8|12.0|14.8|29.1|24.4|22.0|18.1|2.7|3.7|5.4|7.4|10.3|6.9|9.1|12.3|18.2|33.3|52.7|51.5|23.9|
|7.2|2.4|2.7|3.2|3.8|18.3|20.8|22.0|22.5|5.9|7.7|10.3|14.1|20.3|14.0|18.3|25.6|44.1|70.6|76.3|51.8|15.4|
|26.6|7.1|8.9|11.1|14.0|4.8|6.6|9.8|20.5|10.6|11.9|13.7|17.0|24.0|17.9|25.9|35.2|46.6|48.8|37.5|20.2|10.5|
|54.9|17.4|20.3|23.9|28.2|16.8|19.5|23.3|34.1|13.2|15.8|19.3|26.1|42.1|34.0|51.7|88.9|####|####|97.6|45.3|13.6|
|14.0|4.8|5.7|6.5|7.3|32.5|33.9|34.4|35.2|7.0|8.4|10.0|11.7|13.8|8.0|9.0|11.1|17.1|32.8|52.2|45.4|19.9|
|9.9|3.4|3.9|4.4|5.3|8.5|9.7|12.4|16.9|5.3|7.3|9.8|13.0|19.1|16.1|28.7|46.3|59.5|53.2|33.1|15.6|9.3|
|38.5|11.9|13.6|16.1|19.0|6.4|10.0|21.1|40.1|14.6|16.2|17.7|21.4|29.2|19.6|24.7|34.1|54.6|64.9|46.4|20.8|9.0|
|18.4|7.6|9.0|10.2|11.0|22.8|23.6|23.1|29.4|10.3|10.9|11.7|14.4|21.9|16.9|23.8|41.5|65.3|76.0|65.8|38.1|18.3|
|31.2|13.0|16.0|19.4|23.7|12.7|15.9|23.3|33.4|9.4|12.0|14.9|19.3|28.9|20.7|26.9|44.0|76.3|83.2|57.4|24.5|10.3|
|46.9|20.0|24.3|28.3|32.1|26.0|23.9|20.0|18.3|6.5|9.0|12.6|17.1|22.5|14.5|19.0|34.0|59.5|75.2|59.9|27.2|11.2|
|30.9|9.1|10.7|12.9|15.5|34.0|32.4|29.3|28.1|4.9|5.4|6.4|7.6|9.9|6.3|7.2|8.3|9.8|12.4|16.8|19.6|15.1|
| | | | | |18.2|18.2|18.3|23.6|10.2|13.0|16.0|19.6|26.6|19.0|30.2|55.4|81.1|76.7|51.8|21.5|8.6|

| Particle Apo B | | | | | | ANUC Apo B | | | | | | |
|---|---|---|---|---|---|---|---|---|---|---|---|---|
| P IIa | P IIb | P IIIa | P IIIb | P IVa | P IVb | AN I | AN IIa | AN IIb | AN IIIa | AN IIIb | AN IVa | AN IVb |
| 0.0 | 0.0 | 0.0 | 0.0 | 0.0 | 0.0 | 0.0 | 0.0 | 0.0 | 0.0 | 0.0 | 0.0 | 0.0 |
| 11.5 | 15.6 | 13.4 | 6.0 | 9.4 | 9.7 | 15.3 | 10.0 | 29.9 | 11.1 | 4.4 | 2.8 | 1.4 |
| 12.0 | 18.6 | 11.1 | 3.2 | 7.0 | 13.1 | 8.1 | 8.8 | 31.7 | 11.5 | 4.4 | 3.5 | 4.0 |
| 23.7 | 38.3 | 22.6 | 2.9 | 3.2 | 1.8 | 31.2 | 20.2 | 52.8 | 8.6 | 2.2 | 0.9 | 0.2 |
| 20.0 | 40.5 | 39.2 | 3.2 | 1.7 | 0.0 | 20.5 | 13.0 | 55.0 | 26.5 | 8.5 | 2.5 | 1.0 |
| 15.7 | 33.6 | 41.5 | 9.0 | 4.9 | 3.8 | 18.5 | 12.4 | 53.6 | 28.1 | 9.7 | 2.8 | 0.9 |
| 14.7 | 16.3 | 8.7 | 3.2 | 2.6 | 1.0 | 15.1 | 10.6 | 27.9 | 5.9 | 1.8 | 0.6 | 0.1 |
| 7.1 | 15.8 | 21.0 | 11.5 | 9.4 | 13.2 | 9.8 | 5.7 | 26.1 | 24.0 | 10.8 | 6.4 | 4.2 |
| 11.6 | 24.0 | 18.1 | 3.1 | 5.7 | 6.5 | 20.1 | 8.7 | 34.3 | 15.5 | 4.9 | 1.8 | 0.7 |
| 14.3 | 17.5 | 11.5 | 3.8 | 7.3 | 13.3 | 14.6 | 10.8 | 32.3 | 11.4 | 4.7 | 4.2 | 4.0 |
| 26.7 | 17.6 | 8.2 | 3.4 | 2.4 | 1.4 | 29.6 | 15.2 | 34.9 | 4.7 | 1.5 | 0.8 | 0.3 |
| 20.4 | 25.3 | 13.0 | 4.4 | 6.0 | 5.5 | 19.4 | 14.7 | 43.2 | 9.0 | 2.4 | 1.1 | 0.2 |
| 12.4 | 20.0 | 45.9 | 16.7 | 9.9 | 9.5 | 17.7 | 7.4 | 44.1 | 40.7 | 15.8 | 4.8 | 1.5 |
| 16.4 | 31.5 | 36.3 | 5.9 | 6.4 | 3.7 | 23.3 | 9.7 | 42.1 | 30.3 | 11.5 | 3.8 | 1.2 |
| 12.1 | 21.3 | 16.6 | 4.8 | 8.3 | 9.6 | 12.7 | 9.8 | 36.4 | 14.3 | 5.3 | 3.2 | 1.3 |
| 20.7 | 26.9 | 18.8 | 4.8 | 6.6 | 6.1 | 14.5 | 10.4 | 44.2 | 20.8 | 7.3 | 2.6 | 1.2 |
| 8.4 | 13.0 | 22.7 | 18.0 | 13.5 | 19.8 | 15.7 | 6.1 | 25.8 | 30.3 | 14.8 | 9.5 | 3.8 |
| 0.0 | 0.0 | 0.0 | 0.0 | 0.0 | 0.0 | 0.0 | 0.0 | 0.0 | 0.0 | 0.0 | 0.0 | 0.0 |
| 0.0 | 0.0 | 0.0 | 0.0 | 0.0 | 0.0 | 0.0 | 0.0 | 0.0 | 0.0 | 0.0 | 0.0 | 0.0 |
| 34.0 | 15.9 | 6.6 | 1.2 | 1.3 | 0.0 | 32.0 | 16.7 | 35.6 | 3.3 | 1.0 | 0.8 | 0.6 |
| 10.2 | 16.3 | 12.6 | 3.4 | 3.7 | 5.4 | 23.4 | 6.8 | 20.0 | 9.8 | 4.4 | 3.1 | 1.6 |
| 13.7 | 22.4 | 22.9 | 4.3 | 5.9 | 8.2 | 15.6 | 9.2 | 38.7 | 17.7 | 6.0 | 2.9 | 1.8 |
| 12.0 | 20.4 | 19.2 | 3.8 | 6.2 | 7.2 | 14.5 | 9.2 | 35.9 | 13.7 | 4.1 | 2.0 | 1.5 |
| 4.0 | 7.2 | 11.6 | 13.3 | 16.0 | 5.9 | 5.6 | 2.6 | 13.6 | 22.3 | 11.0 | 5.1 | 2.7 |
| 13.9 | 15.4 | 10.1 | 3.4 | 6.5 | 10.6 | 14.2 | 9.8 | 29.1 | 9.8 | 3.8 | 3.2 | 3.1 |
| 15.9 | 25.1 | 47.5 | 6.1 | 5.0 | 5.7 | 11.3 | 5.3 | 27.5 | 44.9 | 22.2 | 10.3 | 5.4 |
| 13.8 | 21.4 | 35.2 | 3.7 | 5.4 | 7.8 | 13.0 | 6.3 | 34.7 | 31.7 | 12.8 | 3.8 | 1.6 |
| 15.1 | 24.2 | 16.7 | 3.0 | 4.4 | 3.8 | 17.0 | 8.8 | 32.7 | 14.5 | 5.1 | 2.6 | 2.4 |
| 35.9 | 58.7 | 23.0 | 6.3 | 6.8 | 5.3 | 27.4 | 19.0 | 79.2 | 30.6 | 9.7 | 2.9 | 1.2 |
| 0.0 | 0.0 | 0.0 | 0.0 | 0.0 | 0.0 | 0.0 | 0.0 | 0.0 | 0.0 | 0.0 | 0.0 | 0.0 |
| 23.1 | 18.5 | 8.8 | 2.1 | 2.3 | 2.7 | 15.1 | 11.0 | 37.7 | 11.5 | 3.7 | 2.2 | 1.8 |
| 13.1 | 22.7 | 26.2 | 4.4 | 4.8 | 4.1 | 18.4 | 8.5 | 38.5 | 16.8 | 5.2 | 2.3 | 1.3 |
| 15.6 | 27.7 | 33.4 | 9.8 | 9.2 | 14.1 | 17.0 | 11.3 | 49.6 | 28.2 | 10.3 | 5.0 | 2.6 |
| 12.1 | 24.9 | 27.6 | 4.6 | 5.0 | 11.6 | 17.2 | 9.9 | 45.8 | 18.4 | 5.5 | 2.3 | 0.9 |
| 15.3 | 30.8 | 27.2 | 5.1 | 7.0 | 9.7 | 15.7 | 9.5 | 47.3 | 24.4 | 7.6 | 3.1 | 2.2 |
| 6.0 | 9.7 | 13.9 | 12.1 | 22.5 | 10.5 | 13.8 | 4.9 | 18.0 | 21.4 | 11.5 | 8.9 | 4.5 |
| 26.2 | 44.0 | 21.3 | 2.5 | 3.4 | 3.9 | 20.0 | 14.6 | 56.2 | 19.3 | 5.7 | 2.3 | 1.0 |

FIGURE 6

METHOD FOR IDENTIFYING AT RISK CARDIOVASCULAR DISEASE PATIENTS

This application claims priority of U.S. application Ser. No. 10/122,081, filed Apr. 12, 2002, now U.S. Pat. No. 6,812,033, issued on Nov. 2, 2004, and provisional application 60/390,796 filed Jun. 21, 2002, both applications are incorporated herein by reference in their entirety.

FIELD OF THE INVENTION

This invention is in the field of cardiovascular healthcare management and patient treatment.

BACKGROUND OF THE INVENTION

According to the National Cholesterol Education Program (NCEP) guidelines, low density lipoprotein (LDL) cholesterol goals and criteria for Therapeutic Lifestyle Changes and Drug Therapy in different risk categories are as follows:

| Risk Category CHD or CHD | LDL Goal | LDL level to initiate Therapeutic Lifestyle Changes | LDL level to consider Drug Therapy |
|---|---|---|---|
| Risk Equivalents | <100 mg/dL | ≧100 mg/dL | ≧130 mg/dL(10 yr risk 10-20%) ≧160 mg/dL(10-yr risk <10%) |
| 2+ Risk Factors | <130 mg/dL | ≧130 mg/dL | ≧130 mg/dL(10 yr risk 10-20%) ≧160 mg/dL(10-yrrisk <10%) |
| 0-1 Risk Factor | <160 mg/dL | ≧160 mg/dL | ≧190 mg/dL |

The invention utilizes the health care management system described in WO 01/41037A3 to study data from patient populations for cardiovascular risk factors especially those factors related to LDL and HDL subclasses. WO 01/41037AC is incorporated herein in its entirety. The text, Heart Disease Breakthrough, by Thomas Yannios, M.D. John Wiley & Son, Inc., New York, 1999 discusses management of heart disease and the role of HDL and LDL subclasses and is incorporated herein by reference.

Williams, PT, Superko, HR, Alderman EA, Small Low Density Lipoprotein III but not Low Density Lipoprotein Cholesterol is Related to Arteriographic Progression, Circulation 2000; 102:II-848

BRIEF DESCRIPTION OF THE DRAWINGS

FIG. 1 shows chemistry values for whole blood plasma.
FIG. 2 shows ANUC data for HDL subfractions.
FIG. 3 shows ANUC data for LDL subfractions
FIG. 4 shows ANUC lipoprotein mg/dl and ANUC subclass %
FIG. 5 shows transidyne subclass %, calculated subclass % and Mass ApoB data
FIG. 6 shows particle ApoB and ANUC ApoB data

SUMMARY OF THE INVENTION

Figure 7:
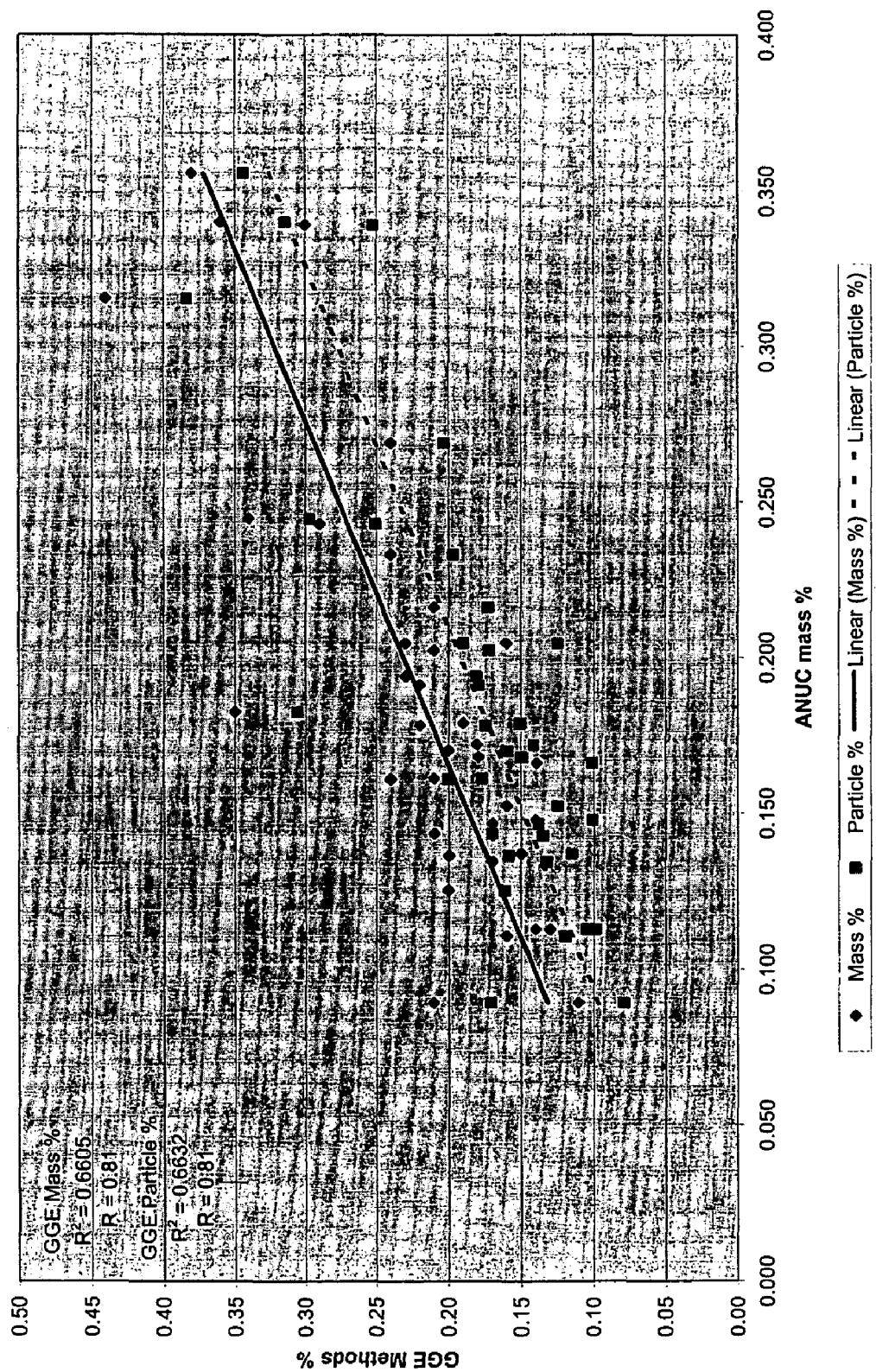
FIG. 7 shows ANUC mass % vs. GGE methods % for LDL I
Figure 8:
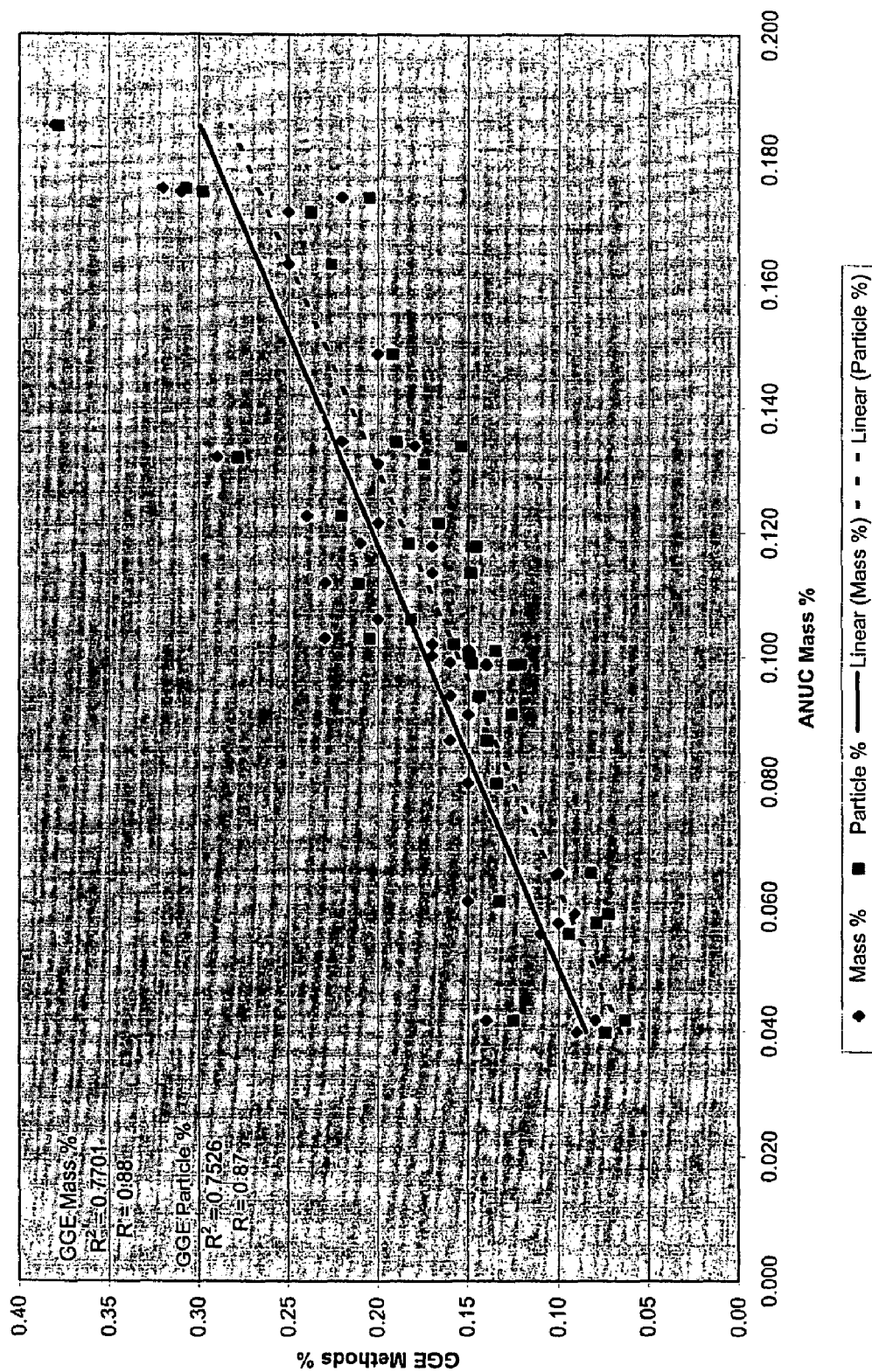
FIG. 8 shows ANUC mass % vs. GGE methods % for LDL IIa
Figure 9:
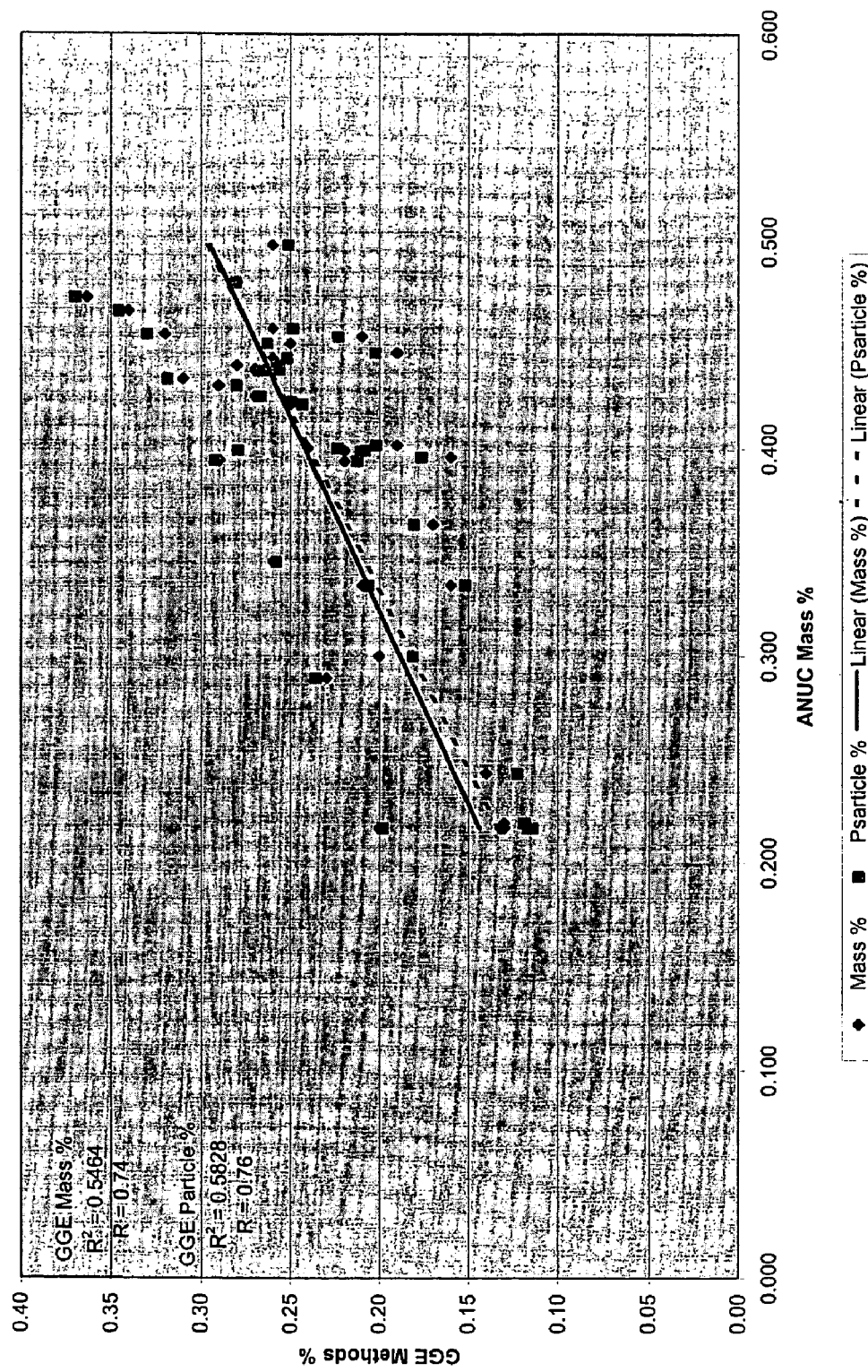
FIG. 9 shows ANUC mass % vs. GGE methods % for LDL IIb
Figure 10:
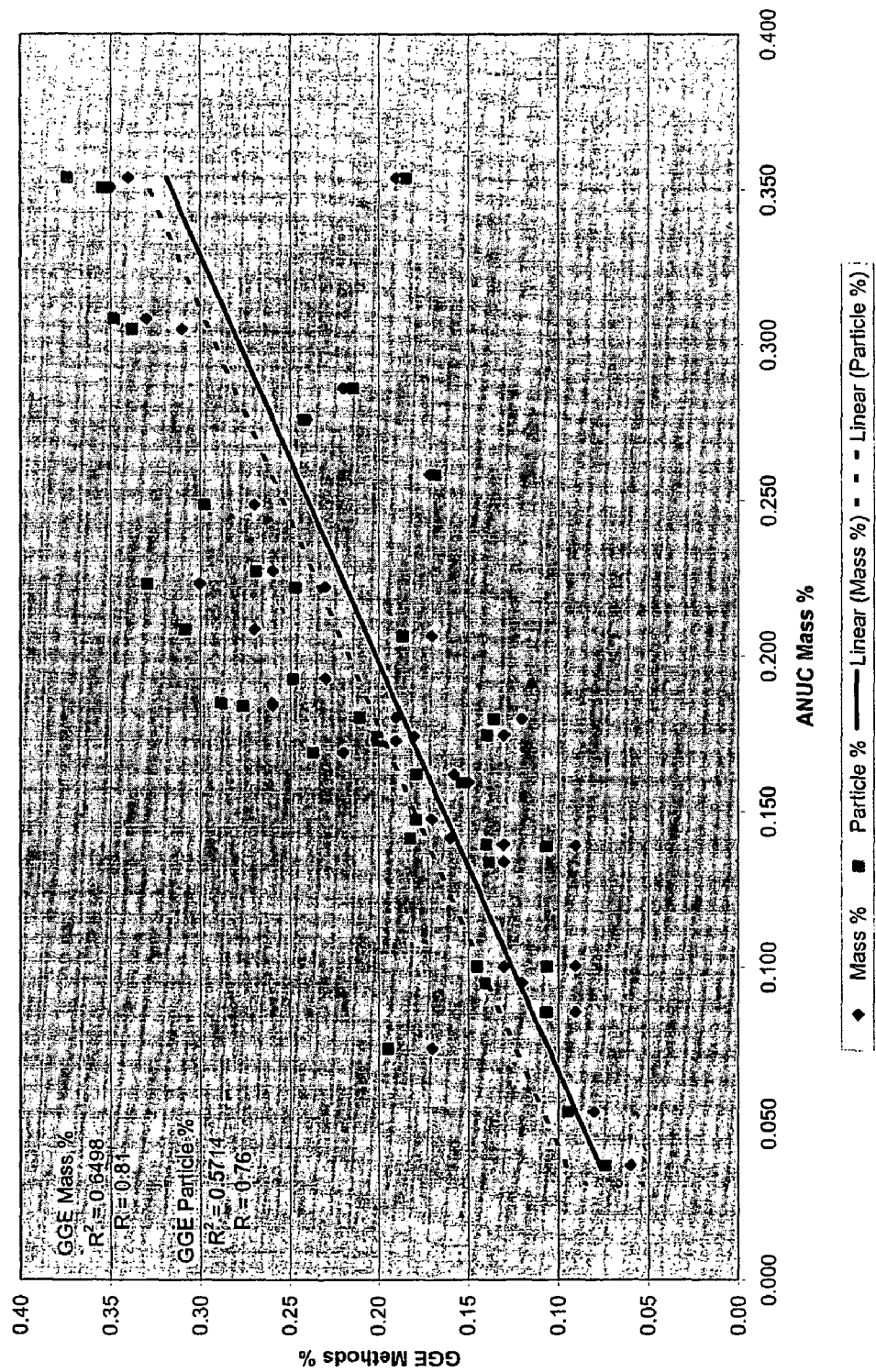
FIG. 10 shows ANUC mass % vs. GGE methods % for LDL IIIa
Figure 11:
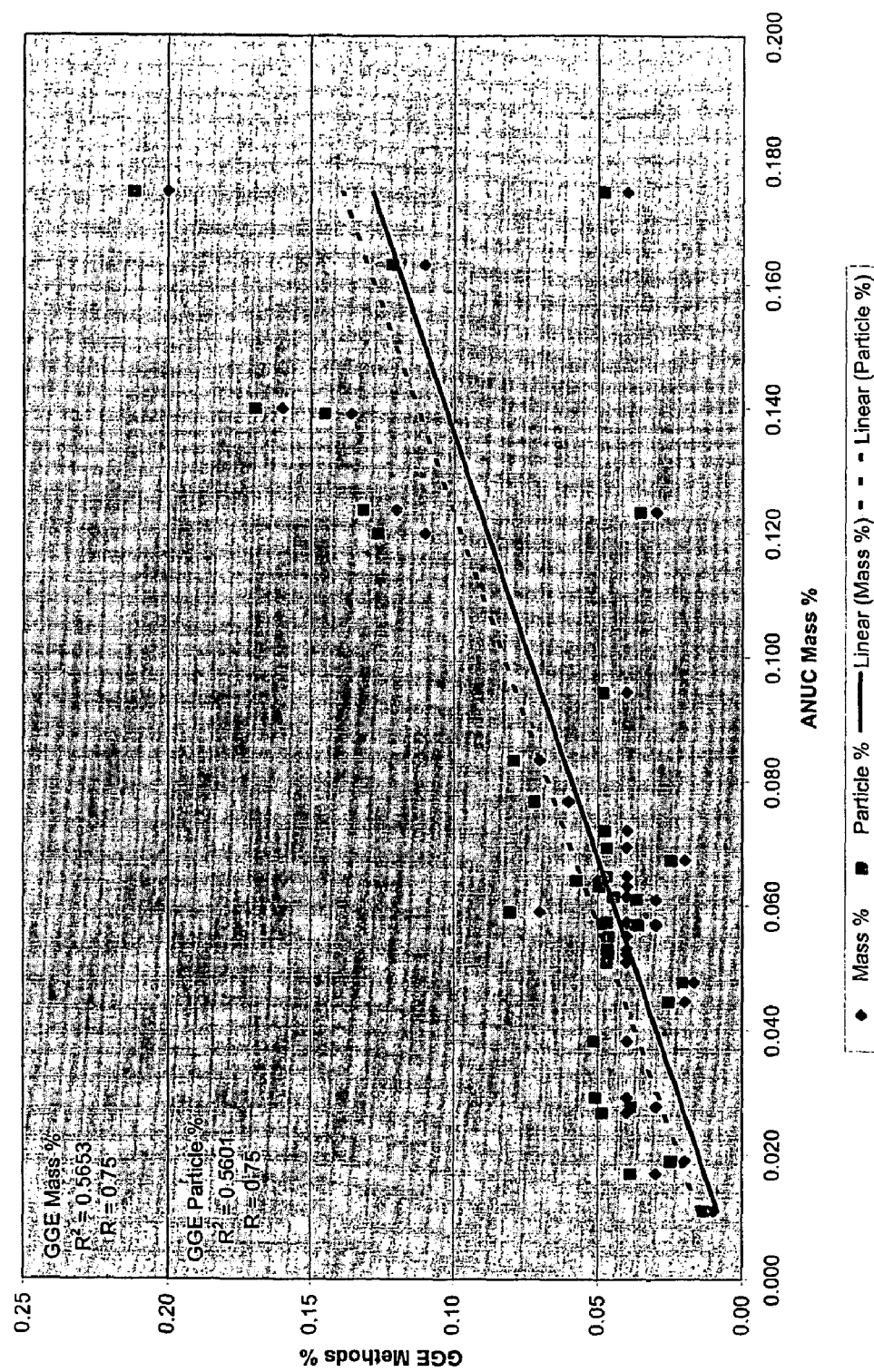
FIG. 11 shows ANUC mass % vs. GGE methods % for LDL IIIb
Figure 12:
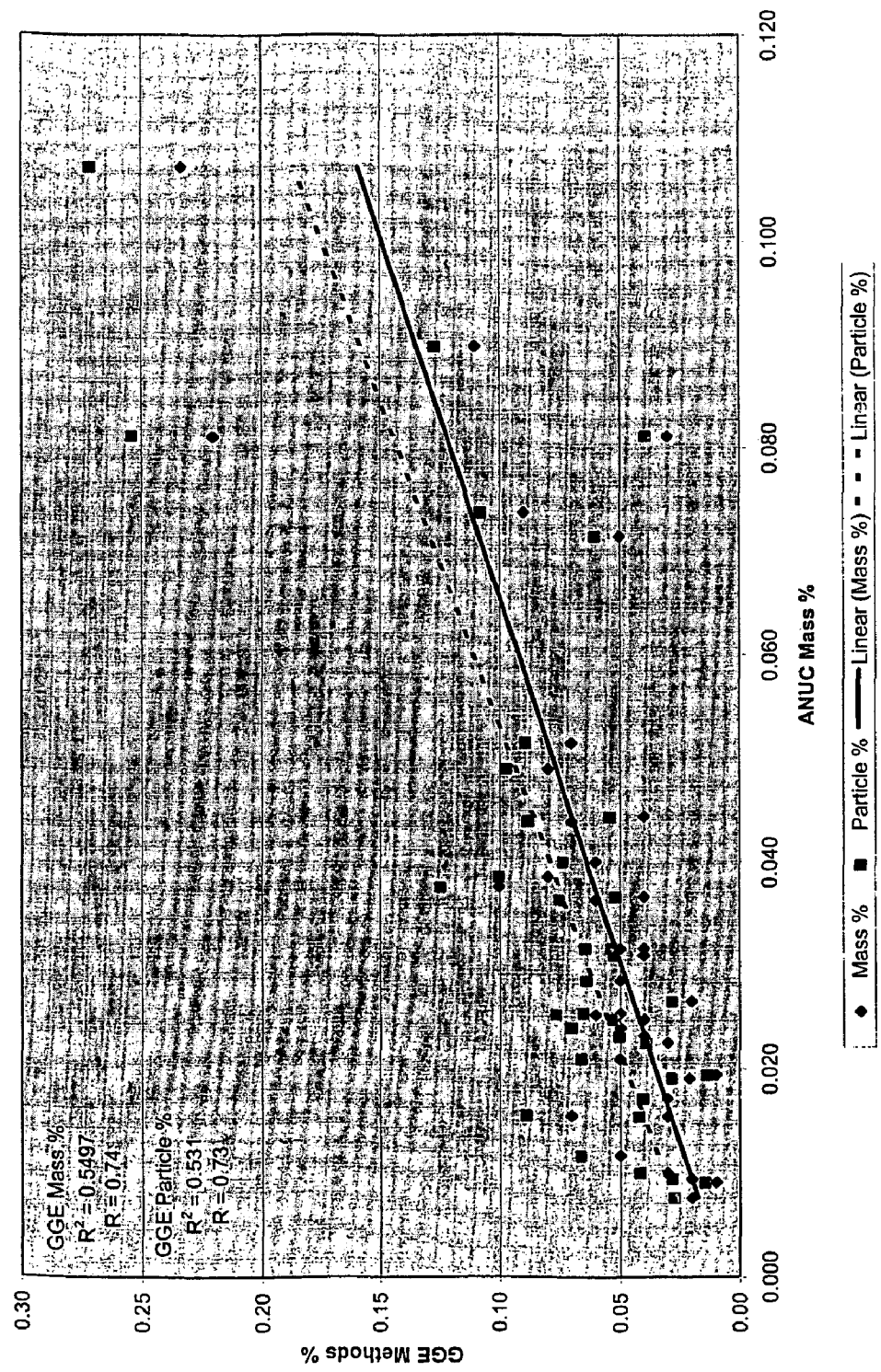
FIG. 12 shows ANUC mass % vs. GGE methods % for LDL IVa
Figure 13:
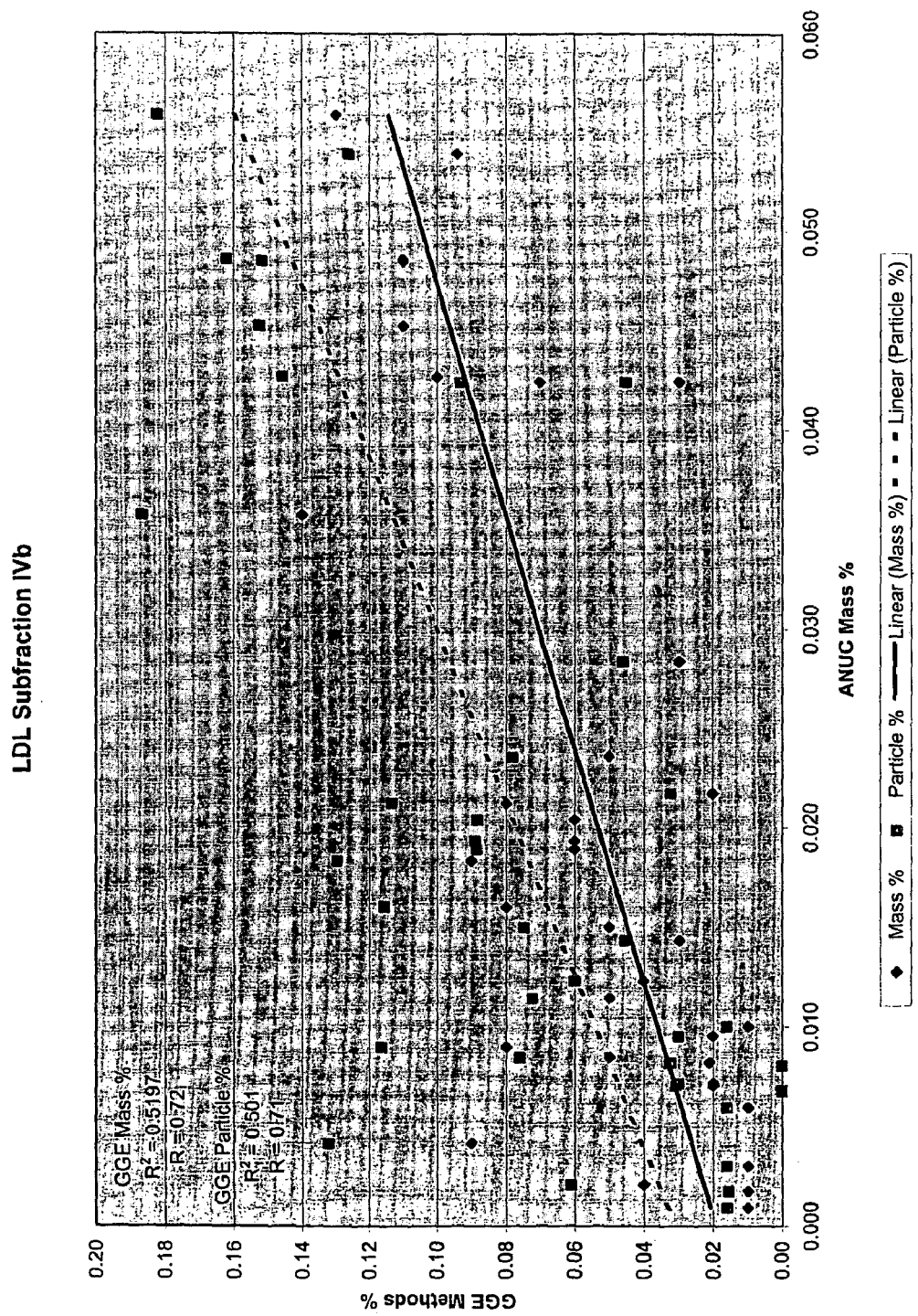
FIG. 13 shows ANUC mass % vs. GGE methods % for LDL IVb

The invention provides a data base of LDL, I, Ia, IIb, IIIa, IIb, IVa, IVb and HDL2a, HDL2b, HDL 3a, HDL 3b and HDL 3c together with patient data such as HDL-C, LDL-C, Apo A, ApoB, Lp(a) and patient personal data useful for treatment, diagnosing, and monitoring cardiovascular disease. The data base contains the LDL and HDL subfraction data in quantitative mg/dl values and permits deriving relationship amongst the LDL and HDL values and cardiovascular disease. Quantitative data permits more effective treatment and monitoring of cardiovascular disease. For example, quantitative differences in LDL and HDL subclass levels can determine the need for more or less aggressive treatment. The data base which includes patient events, procedures, interventions which is correlated to LDL and HDl quantitative subclass data permits development of personalized patient treatment plans and monitoring the effectiveness of such treatment. Thus, LDL and HDL quantitative subfraction data can be used to more effectively treat and monitor cardiovascular disease.

The subfraction levels may be identified by any means such as per cent distribution of the subfraction levels or with quantitation such as concentration of a subfraction level or with the size of the predominant lipoprotein molecules. Once a patient has been identified (diagnosed), the method is used to generate an individualized treatment plan for the patient that may include drugs, diet and exercise.

The invention includes a data base for LDL and HDL subclasses in mg/dl and data for cardiovascular disease patients. This data base permits correlation of LDL and HDL subclass determination in patients with cardiovascular disease and therefore the diagnosis of cardiovascular disease and the monitoring of cardiovascular disease and therapy of such disease. The data base may contain data for related LDL and HDL subclasses in mg/dl which are correlated to cardiovascular disease.

In analyzing LDL and HDL subclass data from more than 65,000 cardiovascular patients, it has been found that indicia for patient treatment can be derived from LDL and HDL subclass information that is not available from NCEP risk factor data. Thus, the invention permits the identification of patients with healthy low density lipoprotein concentration (LDLC) and high density lipoprotein concentration (HDLC) levels who have an undesirable small dense LDL trait and/or deficient reverse cholesterol transport system. For example, it has unexpectedly been found that the determination of LDL III a & b permits the identification of patients who are in need of therapeutic lifestyle changes and/or drug therapy which are not evident from NCEP guidelines based on a conventional panel of lipid assays. Similarly HDL 2b values can be used to identify patients in need of lifestyle change or drug therapy. LDL III a & b and HDL 2b values combined is a powerful tool for identifying patients who need treatment which NCEP data indicate are not in need of treatment.

More specifically, it has been determined that cardiovascular patients with LDL III a & b levels, small dense LDL particles, of about 15% or more are in need of more aggressive cardiovascular healthcare management, i.e., lifestyle changes and/or drug therapy. This LDL III a & b measurement identifies about 40% of patients in need of treatment that are missed by only using NCEP guidelines. Thus, the NCEP guidelines for treatment which are based on the basic lipid panel described above are not capable of efficiently determining cardiovascular risk in a significant subpopulation of patients and result in not treating at risk cardiovascular patients.

The invention therefore encompasses a method for identifying patients with normal NCEP lipid levels who are in need of treatment for cardiovascular disease measuring one or more LDL or HDL particle subfraction levels and identifying abnormal LDL or HDL subfraction levels. The subfraction levels may be identified by any means such as per cent distribution of the subfraction levels or with quantitation such as concentration of a subfraction level or with the size of the predominant lipoprotein molecules. Once a patient has been identified (diagnosed), the method is used to generate an individualized treatment plan for the patient that may include drugs, diet and exercise. The method of the invention can be used to tailor the degree of aggressiveness of patient treatment, as well as, monitoring the patient's treatment.

In analyzing LDL and HDL subclass data from more than 80,000 cardiovascular patients, it has been found that indicia for patient treatment can be derived from LDL and HDL subclass information that is not available from NCEP risk factor data. Thus, the invention permits the identification of patients who have an undesirable small dense LDL trait and deficient reverse cholesterol transport system. For example, it has unexpectedly been found for the first time that elevated LDL-IVb levels are predictive of the need for multiple invasive cardiac procedures. This analysis indicates that in patients requiring invasive cardiac procedures who have a high amount of LDL distribution in the IVb region are likely to need repeated invasive procedures despite lower LDL-C values. A metabolic profile characterized by an abundance of the smallest LDL particles appears to increase the risk of a patient for a need for repeated cardiovascular procedures.

Thus, the invention relates to identifying patients who will or who have had an invasive cardiovascular procedure who have a LDL IVb level greater than 10% of the LDL particles.

LDL III a+b are the preferred LDL subclasses to be measured and HDL 2b is the preferred HDL subclass. Other factors such as lipoprotein (a) (Lp(a)), triglycerides, and homocysteine also provide highly useful information. LDL and HDL subclasses are determined by segmented gradient gel electrophoresis (GGE), NMR, ultracentrifugation, or ion mobility analysis. The LDL and HDL values are converted to mg/dL.

Annual rate of stenosis change was related concordantly to on-study averages of total cholesterol (p=0.04), triglycerides (p=0.05), VLDL-mass (p=0.03), total HDLC ratio (p=0.04), LDL-IVb (p=0.01) and HDL3a (p=0.02) and inversely to HDL2 mass (p=0.02) and HDL2b (p=0.03). Adjustment for other lipid and liporotein factors including most other lipoprotein subclasses, did not eliminate the significant association between LDL-IVb and the annual rate of stenosis change. Stepwise multiple regression analysis showed that the best fitting model for predicting stenosis change included only one lipoprotein variable; LDL-IVb. The average annual rate in stenosis change was six-fold more rapid in the fourth quartile of LDL-IVb (>5.2%) than in the first quartile (>2.5%, p=0.03).

LDL IVb subclass may be determined by linear gel electrophoresis, segmented gradient gel electrophoresis (GGE), NMR, analytical ultracetrifugation, or ion mobility analysis.

EXAMPLE 1

Identifying At Risk Cardiovascular Disease Patients

Database Statistics:
There are 65,536 patients in the database of which 51% (33,463) have LDLC<130 mg/dL and 44% (20,149) have levels of LDLC<100 mg/dL. Furthermore, 47% (31,102) of all patients in the database have LDL IIIa+b measurements.

Methods:
Database search criteria was set at two LDL levels: patients with LDLC<130 and patients with LDLC<100.

Results:
Of the patients with LDLC<130 and measured LDL- by segmented gradient gel electrophoresis (GGE), 74% had an LDL IIIa+b >15% (see below)—a value documented to raise cardiovascular risk by 3-fold.

A. LDLC<130 mg/dL =33, 463 patients (51% of total volume)
  1. LDLC <130 mg/dL with LDLIIIa+b>15%=74%
  2. LDLC <130 mg/dL with LDLIIIa+b>20%=55%
    3. Pheno A=19,653 or 44%
    4. Pheno AB=5,568 or 17%
    5. Pheno B=13,173 or 39%
    **Note: Each database has a limiting population factor. The above search only uses two variables and the limiting factor is LDLIIIa+b (n=18,797). Each introduction of a new variable limits the population of the result.

Of the patients with LDLC<100 and measured LDL-GGE, 85% of them had a LDL IIIa+b>15%(see below).

B. LDLC<100 mg/dL=20,149 patients (44% of total volume)
  1. LDLC<100 mg/dL with LDLIIIa+b>15%=85%
  2. LDLC<100 mg/dL with LDLIIIa+b>20%=70%
    3. Pheno A=8,411 or 42%
    4. Pheno AB=3,431 or 17%
    5. Pheno B=8,307 or 41%

In either case, patients considered to be under "control" and thought not to require further treatment by NCEP guidelines had a preponderance of small, dense atherogenic particles and required varying degrees of aggressive treatment.

Another aspect of the invention involves utilizing the HDL 2b subclass data in the database. If the LDLC<100 database is used, the invention provides a test for hard to treat or difficult patients. But, the LDL<100 database also illustrates that just driving down LDLC is not always the solution. On the other hand, the LDL<130 database may seem too conservative because the NCEP goal is 100 for patients with CHD or CHD risk equivalents, but it does adhere to the population of patients who have family history or haven't been treated and need to establish a baseline to monitor therapy. The four variable search of patients with LDLC<130, HDL>40, an LDL IIIa+b value, and/or an HDL 2b value exhibits similar results from the LDLC<130 database.

C. LDLC<130 mg/dL+HDLC>40 mg/dL=13,810
  1. (C) with LDLIIIa+b>15%=70%
  2. (C) with LDLIIIa+b>20%=43%
  3. (C) with HDL 2b>20%=56%
  4. (C) with LDLIIIa+b>15%+HDL 2b>20%=59%
  5. (C) with LDLIIIa+b>20%+HDL 2b>20%=40%

If it is assumed these patients have 2+ risk factors, the LDLC<130 and HDL>40 are at "healthy" levels according to NCEP, but the same verdict is displayed as the above database search. 70% of the population has an elevated LDL IIa+b. When HDL 2b is added to the equation, the percentage of patients with both abnormal LDL IIIa+b and HDL 2b values slightly lessen to 59%. Thus, about 6 out of 10 patients with "healthy" LDLC and HDLC levels express both the small dense LDL trait and deficient reverse cholesterol transport system.

The other four variable search of patients with LDLC<100, HDL>40, an LDL IIIa+b value, and/or an HDL 2b value exhibits similar results from its database sibling. The concomitant risk factors of elevated LDLIIIa+b and deficient HDL 2b occur 91% of the time.

D. LDLC<100 mg/dL+HDLC>40 mg/dL=11,334
  1. (D) with LDLIIIa+b>15%=84%
  2. (D) with LDLIIIa+b>20%=60%
  3. (D) with HDL 2b>20%=53%
  4. (D) with LDLIIIa+b>15%+HDL 2b>20%=91%
  5. (D) with LDLIIIa+b>20%+HDL 2b>20%=68%

Physicians who have patients with an LDLC value under control (<100) often conclude that they need no further information for treating the patient. This is not the case (See B), 85% of the population with LDL IIIa+b values were elevated and were in need of treatment.

There are several other aspects of the invention derived from the database analysis such as 61% of patients with LDL<100 or LDL<130 and TG<150 still have deficient or abnormal HDL 2b values (LDLC under control and triglyceride metabolism working fine, but unapparent deficient reverse cholesterol transport). All of these newly discovered relationships are summarized below in their respective database (LDLC<130 or LDLC<100).

Database Informatics (LDL<130 mg/dL)

(Total Database Volume: 65,536)

(Total of patients with LDL IIIa+b values: 31,102 (47%))

A. LDLC<130 mg/dL=33,463 patients (73% of total volume
  1. LDLC<130 mg/dL with LDLIIIa+b>15%=74%
  2. LDLC<130 mg/dL with LDLIIIa+b>20%=55%
    a. Pheno A=19,653 or 43%
    b. Pheno AB=5,568 or 17%
    c. Pheno B=13,173 or 39%

B. LDLC<130 mg/dL+HDLC>40 mg/dL=13,810
  1. (B) with LDLIIIa+b>15%=70%
  2. (B) with LDLIIIa+b>20%=43%
  3. (B) with HDL 2b>20%=56%
  4. (B) with LDLIIIa+b>15%+HDL 2b>20%=59%
  5. (B) with LDLIIIa+b>20%+HDL 2b>20%=40%

C. LDLC<130 mg/dL+HDL2b<20%=13,168
  1.(C) with LDLIIIa+b>15%=86%
  2.(C) with LDLIIIa+b>20%=68%

D. LDLC<130 mg/dL+HDL2b>20%=3,642
  1. (D) with LDLIIIa+b>15%=77%
  2. (D) with LDLIIIa+b>20%=38%

E. LDLC<130 mg/dL+HDL2b>20%+Lp(a)>20mg/dL=1,417
  1. (E) with LDLIIIa+b>15%=77%
  2. (E) with LDLIIIa+b>20%=38%

F. LDLC<130 mg/dL+Lp(a)>20mg/dL 10,587
  1. (F) with LDLIIIa+b>15%=73%
  2. (F) with LDLIIIa+b>20%=52%

G. LDLC<130 mg/dL+HDLC>40 mg/dL=11,226
  1. (G) with LDLIIIa+b>15%=70%
  2. (G) with LDLIIIa+b>20%=43%

H. LDLC<130 mg/dL+TG<150 mg/dL=28,270
  1. (H) with LDLIIIa+b>15%=70%
  2. (H) with LDLIIIa+b>20%=42%
  3. (H) with HDL 2b<20%=62%

I. LDLC<130 mg/dL+TG<180 mg/dL 24,796
  1. (L) with LDLIIIa+b>15%=72%
  2. (L) with LDLIIIa+b>20%=46%

J. LDLC<130 mg/dL+TG<180 mg/dL+HDL>40mg/dL=16,723
  1.(J) with LDLIIIa+b>15%=70%
  2.(J) with LDLIIIa+b>20%=30%

K. LDLC<130 mg/dL+TG<180 mg/dL+HDL2b>20%=3,549
  1. (K) with LDLIIIa+b>15%=68%
  2. (K) with LDLIIIa+b>20%=37%

Database Informatics (LDLC<100 mg/dL)

(Total Database Volume: 65,536)

(Total of patients with LDL IIIa+b values: 31,102 (47%))

A. LDLC<100 mg/dL=20,149 patients (44% of total volume)
  1.LDLC<100 mg/dL with LDLIIIa+b>15%=85%
  2.LDLC<100 mg/dL with LDLIIIa+b>20%=70%
    a. Pheno A=8,411 or 42%
    b. Pheno AB=3,431 or 17%
    c. Pheno B=8,307 or 41%

B. LDLC<100 mg/dL+HDLC>40 mg/dL=11,334
  1. (B) with LDLIIIa+b>15%=84%
  2. (B) with LDLIIIa+b>20%=60%
  3. (B) with HDL 2b>20%=53%
  4. (B) with LDLIIIa+b>15%+HDL 2b>20%=91%
  5. (B) with LDLIIIa+b>20%+HDL 2b>20%=68%

C. LDLC<100 mg/dL+HDL2b>20%=2,772
  1. (C) with LDLIIIa+b>15%=88%
  2. (C) with LDLIIIa+b>20%=58%

D. LDLC<100 mg/dL+HDL2b<20%=5,906
  1.(D) with LDLIIIa+b>15%=94%
  2.(D) with LDLIIIa+b>20%=81%

E. LDLC<100 mg/dL+HDL2b>20%+Lp(a)>20mg/dL=901
   1.(E) with LDLIIIa+b>15%=92%
   2.(E) with LDLIIIa+b>20%=63%

F. LDLC<100 mg/dL+Lp(a)>20mg/dL=6,024
   1.(F) with LDLIIIa+b>15%=86%
   2.(F) with LDLIIIa+b>20%=70%

G. LDLC<100 mg/dL+TG<180 mg/dL=14,414
   1.(G) with LDLIIIa+b>15%=84%
   2.(G) with LDLIIIa+b>20%=62%

H. LDLC<100 mg/dL+TG<150 mg/dL 12,513
   1.(H) with LDLIIIa+b>15%=84%
   2.(H) with LDLIIIa+b>20%=60%
   3.(H) with HDL 2b<20%=61%

I. LDLC<100 mg/dL+TG<150 mg/dL+Lp(a)>20 mg/dL=4117
   1.(I) with LDLIIIa+b>15%=85%
   2.(I) with LDLIIIa+b>20%=61%

The LDL and HDL data may be converted to mg/dl and a patient's data in mg/dl may be compared to the diagnostic level of HDL or LDL in mg/dl.

EXAMPLE 2

Identifying Patients Who Will Require Multiple Intensive Cardiovascular Procedures The relationship of elevated LDL IVb in a group of patients who required invasive procedure(s) has been investigated. Methods: 79 (Cardiovascular Disease) CAD patients requiring cardiac intervention procedure, were randomly selected based on LDL IVb>=10% or=<3% of the total LDL distribution. Fasting Triglycerides, LDL-C and HDL-C were determined using enzymatic methods, LDL subclass distribution by S3-segmented gradient gel electrophoresis, and Lp(a), homocysteine, and insulin by immunochemical methods. Resuts: There were no significant differences between groups in regard to age, total cholesterol, Lp(a), Apo B, and fibrinogen. The fasting insulin and hs-CRP values were higher (+149%, p+0.06) and (+221%, p+0.06) in the IVb+>10% group, (see Table 1).

TABLE 1

|  | IVb <= 3% | IVb ≧ 10% | % | P |
|---|---|---|---|---|
| N | 30 | 49 |  |  |
| # procedures | 0.2 ± 0.5 | 1.3 ± 1.6 | +650% | 0.0001 |
| LDL IVb(%) | 1.8 ± 0.8 | 12.7 ± 2.4 | +706% | 0.0001 |
| LDL IVa(%) | 3.5 ± 2.4 | 11.3 ± 4.4 | +323% | 0.0001 |
| Triglycerides (mg/dl) | 116 ± 73 | 314 ± 245 | +271 |  |
| HDL-C (mg/dl) | 50.0 ± 15.6 | 35.7 ± 11.6 | −40% | 0.0001 |
| LDL-C(mg/dl) | 98.0 ± 32 | 76.7 ± 22 | −28% | 0.002 |

Thus, patients who need or who have had an invasive cardiovascular procedure such as angioplasty are monitored for the level of LDL IVb. Levels above 10% of LDL IVb as predictive of patients who will need multiple invasive procedures such as angioplasty. Invasive procedures refer to angioplasty, by-pass and similar invasive procedures to treat cardiovascular disease. The patient's HDL and LDL subclass data may be converted to quantitative mg/dl values and compared to diagnostic values in mg/dl.

EXAMPLE 3

Quantitation of LDL and HDL Sub-fractions.

The gradient gel electrophoresis methodology measures relative percentages of the volume of LDL and HDL particles by sub-fraction and the diameter of those particles are known. Assuming the particles are spherical in shape (an assumption made by analytical ultracentrifugation methods as well), the relative percentage of particle numbers can be calculated by multiplying the percent volume value by a value that represents the relative volume of the particles compared to each other.

Using the values for the boundaries of the LDL subclasses, as listed below, we assume that the mean Angstrom value of the subclass can be used to estimated the average size of the particles in that subclass.

| Subfraction | Upper Boundary (A) | Lower Boundary (A) | Mean Value (A) | Mean Radius |
|---|---|---|---|---|
| I | 285.0 | 272.0 | 278.5 | 139.25 |
| IIa | 272.0 | 265.0 | 268.5 | 134.25 |
| IIb | 265.0 | 256.0 | 260.5 | 130.25 |
| IIIa | 256.0 | 247.0 | 251.5 | 125.75 |
| IIIb | 247.0 | 242.0 | 244.5 | 122.25 |
| IVa | 242.0 | 233.0 | 237.5 | 118.75 |
| IVb | 233.0 | 220.0 | 226.5 | 113.25 |

Specifically for LDL, the actual calculated average volume of a sub-fraction I particle is $4/3\pi r^3$ where r on average is 139.25 Å. The relative proportion of volume of sub-fraction I and sub-fraction IVb is $$4/3\pi(139.25)^3/4/3\pi(113.25)^3$$

which reduces to $(139.25)^3/(113.25)^3 = 2700135.828125/1452494.953125 = 1.859$ So sub-fraction I particles are 1.856 times the volume of sub-fraction IVb particles. The relative volume ratios can be calculated for each of the seven LDL subclasses and the five HDL subclasses because we measure the diameter of the particles. The relative volume ratios for the other LDL sub-classes are:

IIa=1.685; IIb=1.521; IIIa=1.369; IIIb=1.258; IVa=1.153; IVb=1.00.

These values are fixed for every patient. From the diameter of a particle it is the spherical volume, assuming that these particles are in fact reasonable spherical.

For purposes of illustration, if a patient's profile showed that he had only subclass I and IVb particles in a ratio of 50% each and every percent of IVb is given a particle value of 10, then every percent of I is given a value of 10/1.856 or 5.39. In other words a given volume that contains 10 IVb particles will contain 5.39 I particles because the subclass I particles are that much bigger than the subclass IVb particles. The factors to correct the mass subclass percents to particle percents, using the size of the IVb particle as the basic unit, are as follows:

I=0.539; IIa=0.593; IIb=0.657; IIIa=0.730; IIIb=0.795; IVa=0.867; IVb=1.0

To recalculate the LDL particle percentages from the volume percentages, we would take the IVb 50% multiply it by 5.39 to give 26.95. The IVb fraction would have a value of 50.0. Sum these values and use the sum as the denominator to recalculate a percentage now based on relative particle number.

In this example, the total is 76.95. The percentage of particles that are IVb is: (50/76.95)×100=65% and the percentage of particles that are I is: (26.95/76.95)×100=35%

The subclasses of larger particles see a decrease in their % values and the subclasses with smaller particles see an increase in their % values, relative to their mass % values.

If these percentages are then multiplied by the Apo B value, the resulting values will be reasonably accurate representations of the absolute particle numbers of the LDL subclasses. There will be some elevation of all the numbers due to the inclusion of the Apo B from VLDL and IDL. The present studies with Ao B ultra, however indicate that this elevation is less than 10% for triglyceride values of less than 200 mg/dL. If Apo B Ultra numbers are used, the elevation will only be from the IDL fraction.

An actual set of patient values over two visits for a 78 year-old male who had therapeutic intervention between visits are shown in Table 2:

TABLE 2

|  | Dec. 20, 2000 | Apr. 11, 2002 | |
| --- | --- | --- | --- |
| Apo B value | 81 | 88 | |
| I (GGE volume %) | 40.6 | 37.3 | Currently reported % values |
| I ( * mg/dL) | 28.1 | 28.0 | Quantitation mg/dL values |
| IIa (GGE volume %) | 26.5 | 24.0 | Currently reported % values |
| IIa ( * mg/dL) | 20.2 | 19.8 | Quantitation mg/dL values |
| IIb (GGE volume %) | 12.9 | 15.8 | Currently reported % values |
| IIb ( * mg/dL) | 10.9 | 14.4 | Quantitation mg/dL values |
| IIIa (GGE volume %) | 5.6 | 10.7 | Currently reported % values |
| IIIa ( * mg/dL) | 5.2 | 10.9 | Quantitation mg/dL values |
| IIIb (GGE volume %) | 3.3 | 4.1 | Currently reported % values |
| IIIb ( * mg/dL) | 3.4 | 4.5 | Quantitation mg/dL values |
| IVa (GGE volume %) | 6.1 | 4.6 | Currently reported % values |
| IVa ( * mg/dL) | 6.8 | 5.5 | Quantitation mg/dL values |
| IVb (GGE volume %) | 5.0 | 3.5 | Currently reported % values |
| IVb ( * mg/dL) | 6.4 | 4.9 | Quantitation mg/dL values |

* refers to absolute subclass particle number

In this case the value of using absolute apoplipoprotein values is seen in the apparent drop in subclasses I and IIa which are actually much smaller than the mass percentages would indicate. The IIIa value which appears to have not quite doubled looking at the mass percentage values, has in fact more than doubled when viewed in terms of the absolute value of Apo B.

A similar calculation has been done for the HDL subclasses quantitating to the Apo A value which also corresponds to particle number for HDL particles. In this case, because the 2B fraction often tapers off to nothing at the high end, the mean peak particle size for subclass 2B needs to be adjusted closer the lower boundary of the 2B subclass. In this example, the mean particle size for this subclass is estimated at 110.8 A, one-third of the range between the two boundaries.

Using the same process, the correction factors for particle size for HDL are as follows:

2B=0.315; 2A=0.516; 3A=0.712; 3B=0.866; 3C=1.00

For the same 78 year-old male, Table 3 his results for his simultaneously measured HDL subfractions:

TABLE 3

|  | Dec. 20, 2000 | Apr. 11, 2002 | |
| --- | --- | --- | --- |
| Apo AI value | 122 | 158 | |
| 2B (GGE volume %) | 17 | 28 | Currently reported % values |
| 2B (* mg/dL) | 11 | 24 | Quantitation mg/dL values |
| 2A (GGE volume %) | 27 | 25 | Currently reported % values |
| 2A ( * mg/dL) | 28 | 35 | Quantitation mg/dL values |
| 3A (GGE volume %) | 37 | 29 | Currently reported % values |
| 3A ( * mg/dL) | 52 | 56 | Quantitation mg/dL values |
| 3B (GGE volume %) | 15 | 14 | Currently reported % values |
| 3B ( * mg/dL) | 26 | 33 | Quantitation mg/dL values |
| 3C (GGE volume %) | 3 | 4 | Currently reported % values |
| 3C (* mg/dL) | 6 | 11 | Quantitation mg/dL values |

* refers to absolute subclass particle number

This set of values particularly illustrates the advantages of converting the relative mass percentages in to absolute apolipoprotein values. The apparent drop in mass, especially 3A, as judged by the change in the mass percentage is in fact an increase in absolute Apo AI values, masked by the increase in the Apo A value.

A further evaluation of the quantitation of LDL subfractions by this method when compared to values obtained from analytical ultracentrifugation follows.

Analytical ultracentrifugation subdivides the lipid fractions based on their density. Gradient gel electrophoresis separates the lipid fractions by size. While there is a strong correlation between the two, the two characteristics are not identical and do not give identical results. However, comparisons of the two LDL methodologies for 37 samples show the following correlation results; Table 4

TABLE 4

Comparison of density ANUC mg/dL LP vs GGE mg/dL LDLC

|  | I | IIa | IIb | IIIa | IIIb | IVa | IVb |
| --- | --- | --- | --- | --- | --- | --- | --- |
| $R^2$ value | 0.6801 | 0.7127 | 0.7843 | 0.6584 | 0.5306 | 0.3851 | 0.3256 |
| R value | 0.82 | 0.84 | 0.89 | 0.81 | 0.73 | 0.62 | 0.57 |

In this case, the ANUC values are in mg/dL of total lipoprotein mass, and were not measured separately as cholesterol, triglycerides or Apolipoprotein B. The LDL Cholesterol value for the whole plasma sample was used as the best approximation of a measured value that represented only the LDL fraction. All the other measured values are confounded by having significant contributions to their results from the presence of VLDL and chylomicrons.

The Apo B levels for the original samples were measured for the whole plasma sample, but not for each individual ANUC subfraction. The Apo B values for the ANUC subfractions were determined by multiplying the Apo B values by the ANUC mass percentages to give the following table 5:

TABLE 5

Comparison of ANUC Apo B mg/dL vs GGE Apo B mg/dL

| | I | IIa | IIb | IIIa | IIIb | IVa | IVb |
|---|---|---|---|---|---|---|---|
| $R^2$ value | 0.2143 | 0.7543 | 0.8599 | 0.7426 | 0.4545 | 0.4569 | 0.4007 |
| R value | 0.46 | 0.87 | 0.93 | 0.86 | 0.67 | 0.68 | 0.63 |

If the correlation between the mass percentage numbers are used alone the correlation improves, indicating that the density gradient results vs. size gradient results, while overlapping significantly, are not identical as shown in Table 6.

TABLE 6

Comparison of ANUC Mass % vs GGE Mass %

| | I | IIa | IIb | IIIa | IIIb | Iva | IVb |
|---|---|---|---|---|---|---|---|
| $R^2$ value | 0.6605 | 0.7701 | 0.5464 | 0.6498 | 0.5653 | 0.5497 | 0.5197 |
| R value | 0.81 | 0.88 | 0.74 | 0.81 | 0.75 | 0.74 | 0.72 |

Figure 4:
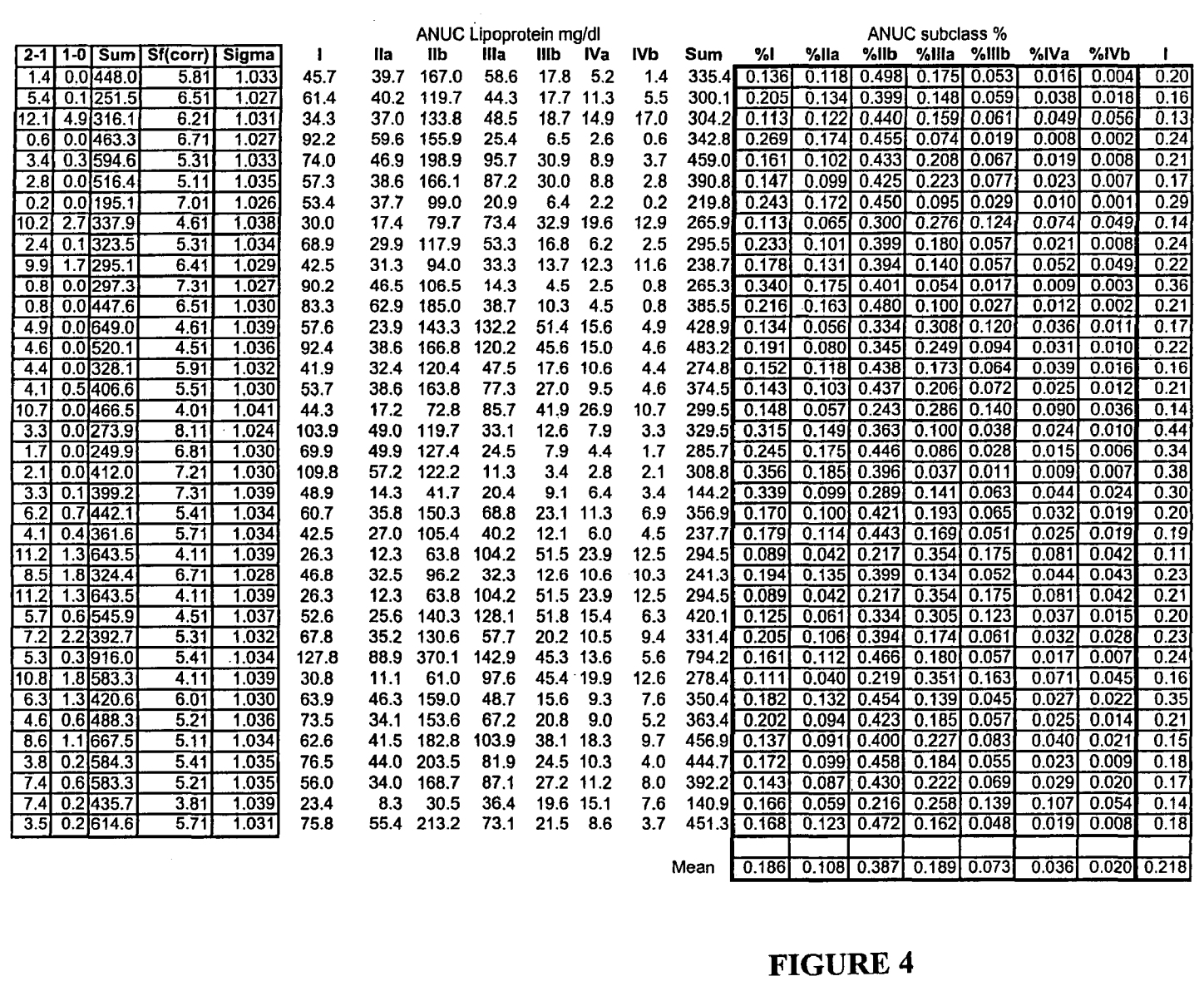
Figure 5:
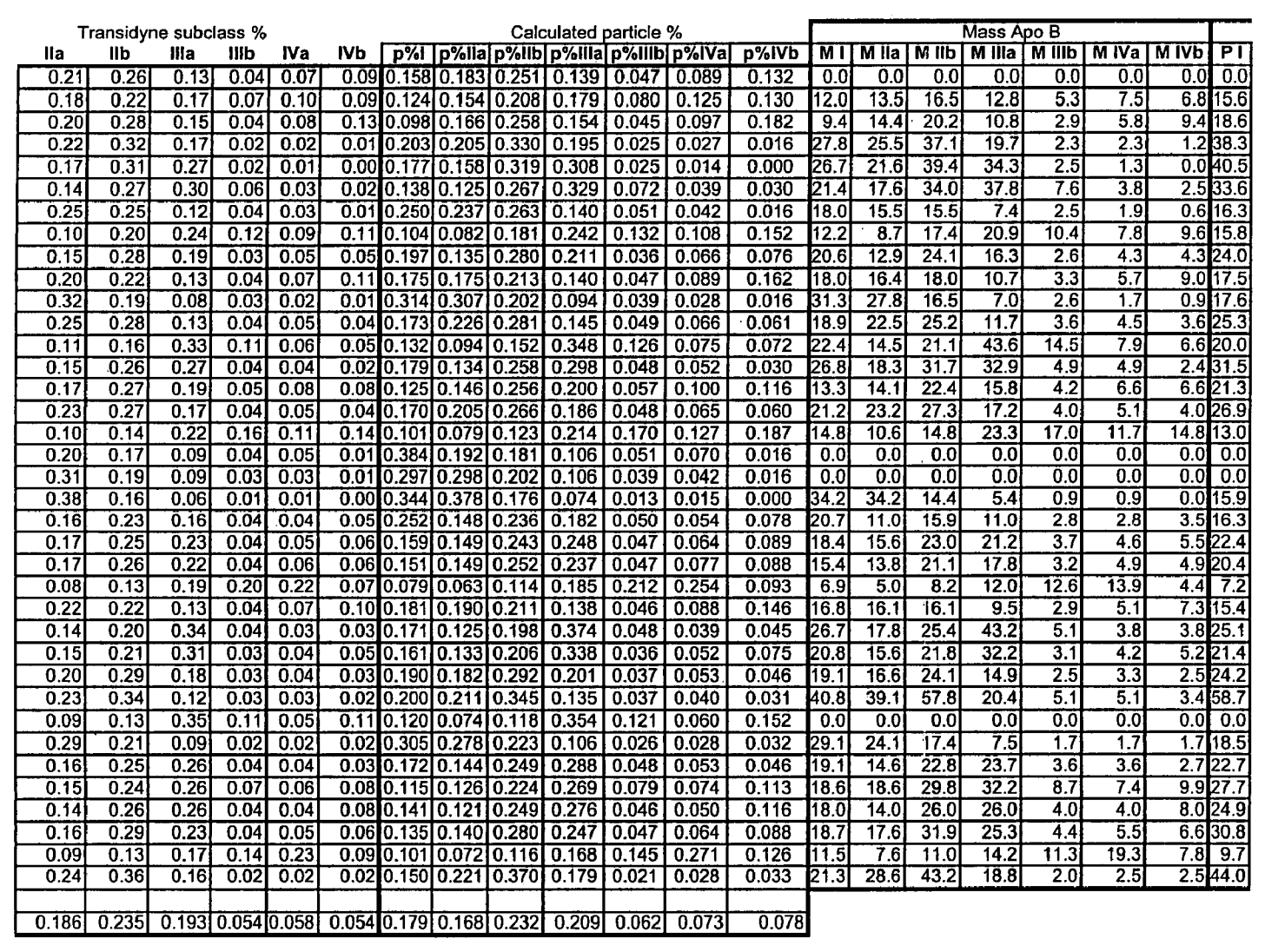

FIG. 1 shows chemical values such as HDL-C, LDL-C, ApoA, ApoB, and LP(a), LDL phenotype, LDL Peak 1 and LDL peak 2 for 38 patients. FIG. 2 shows the ANUC HDL fractions and ANUC total values for these patients and FIG. 3 shows ANUC LDL fraction for the same patients. FIG. 4 shows the ANUC lipoprotein values for LDL subfractions I, Ia, IIb, IIIa, IIIb, IVa, IVb and the % ANUC subclass data. FIG. 5 shows the GGE transidyne subclass percent for I through Wb LDL subfractions, calculated particle percent for these subfractions and ApoB mass values. FIG. 6 shows the particle ApoB and ANUC ApoB LDL subclass data.

FIGS. 7 through 13 shows correlation plots of ANUC values verses two GGE methods for LDL subfractions I, Ia, IIb, IIIa, IIIb, IVa, IVb.

Figure 14:
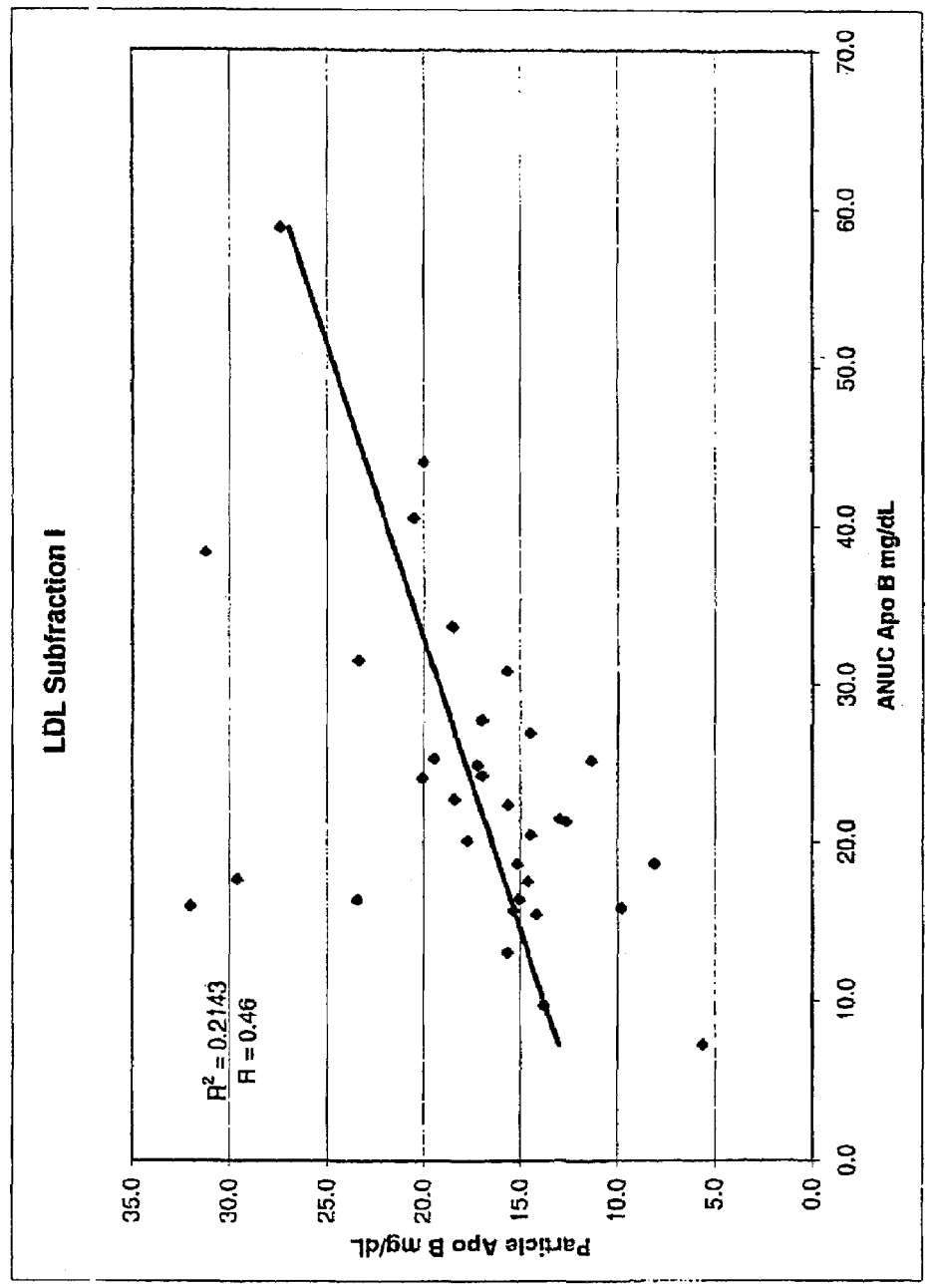
FIG. 14 shows ANUC Apo B mg/dl vs. particles ApoB mg/dl for LDL I
Figure 15:
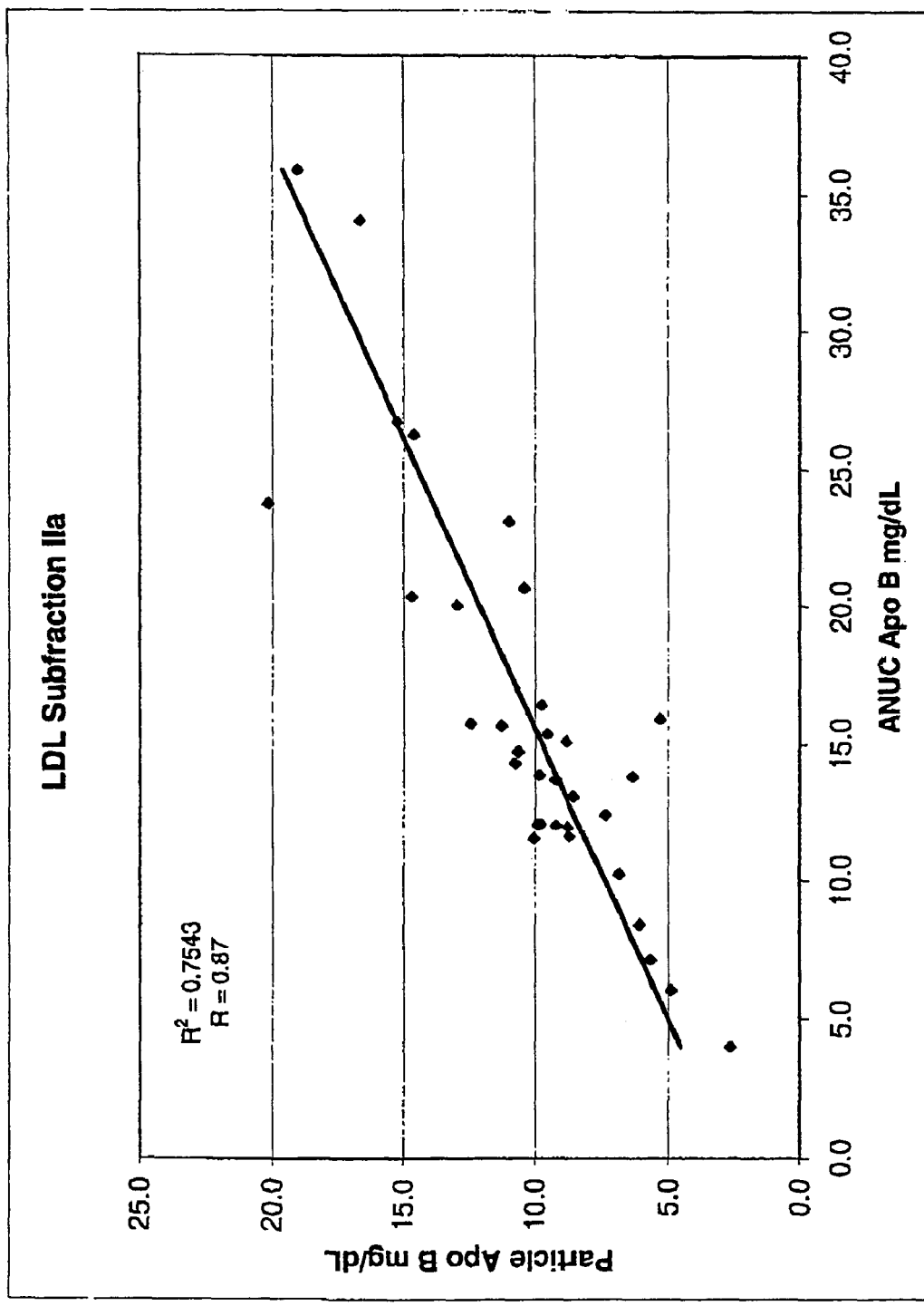
FIG. 15 shows ANUC Apo B mg/dl vs. particles ApoB mg/dl for LDL Ia
Figure 16:
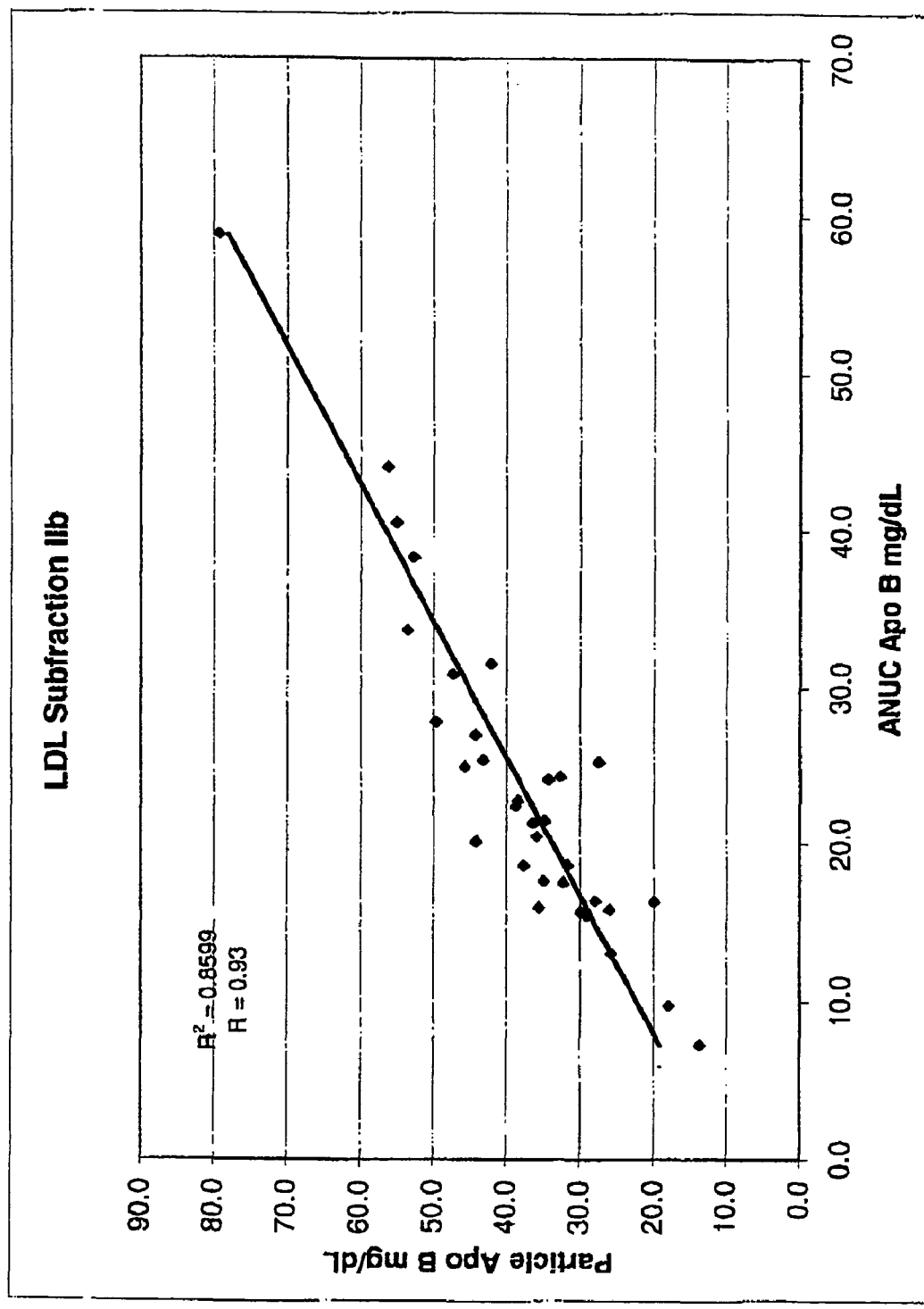
FIG. 16 shows ANUC Apo B mg/dl vs. particles ApoB mg/dl for LDL IIb
Figure 17:
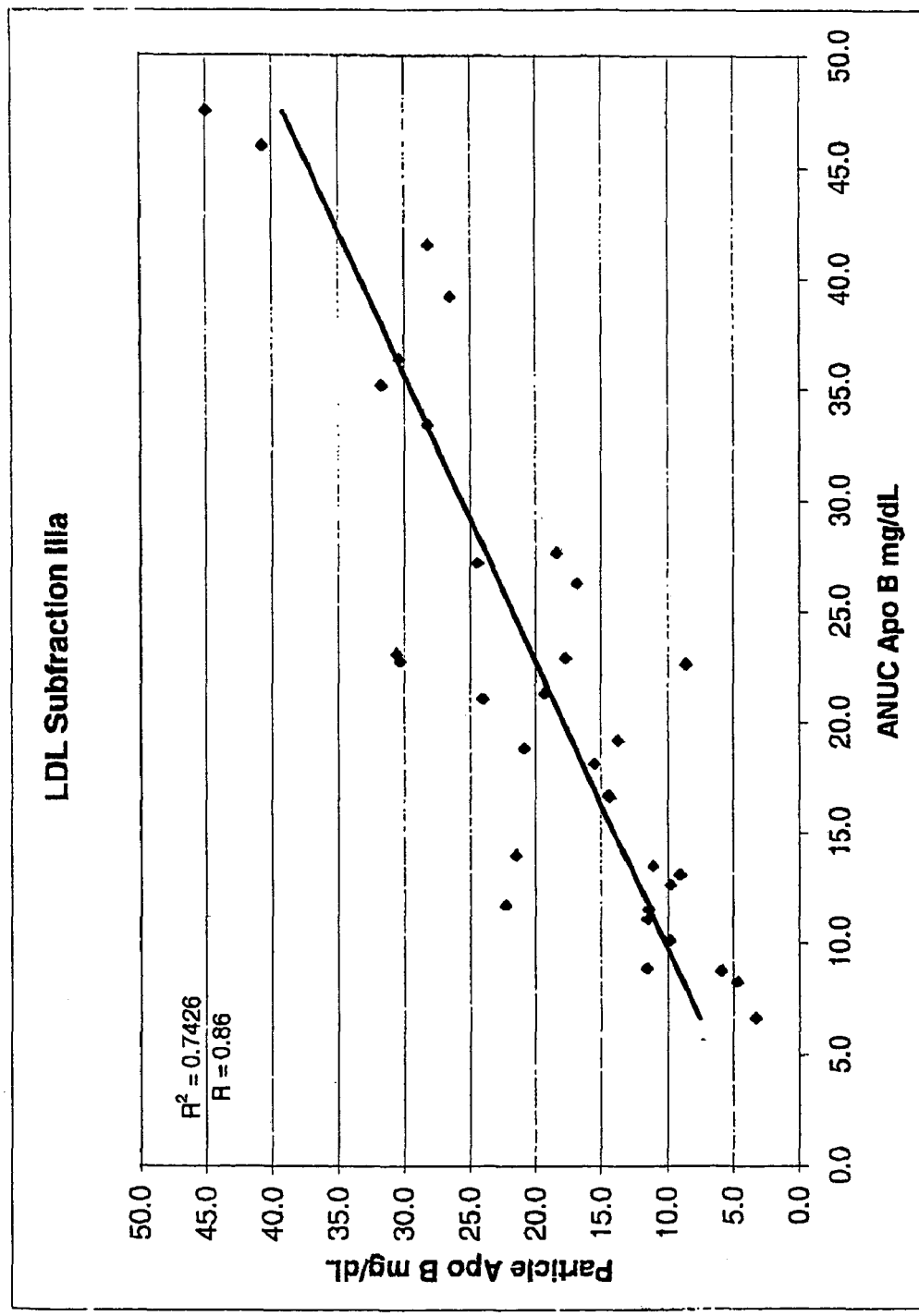
FIG. 17 shows ANUC Apo B mg/dl vs. particles ApoB mg/dl for LDL IIIa
Figure 18:
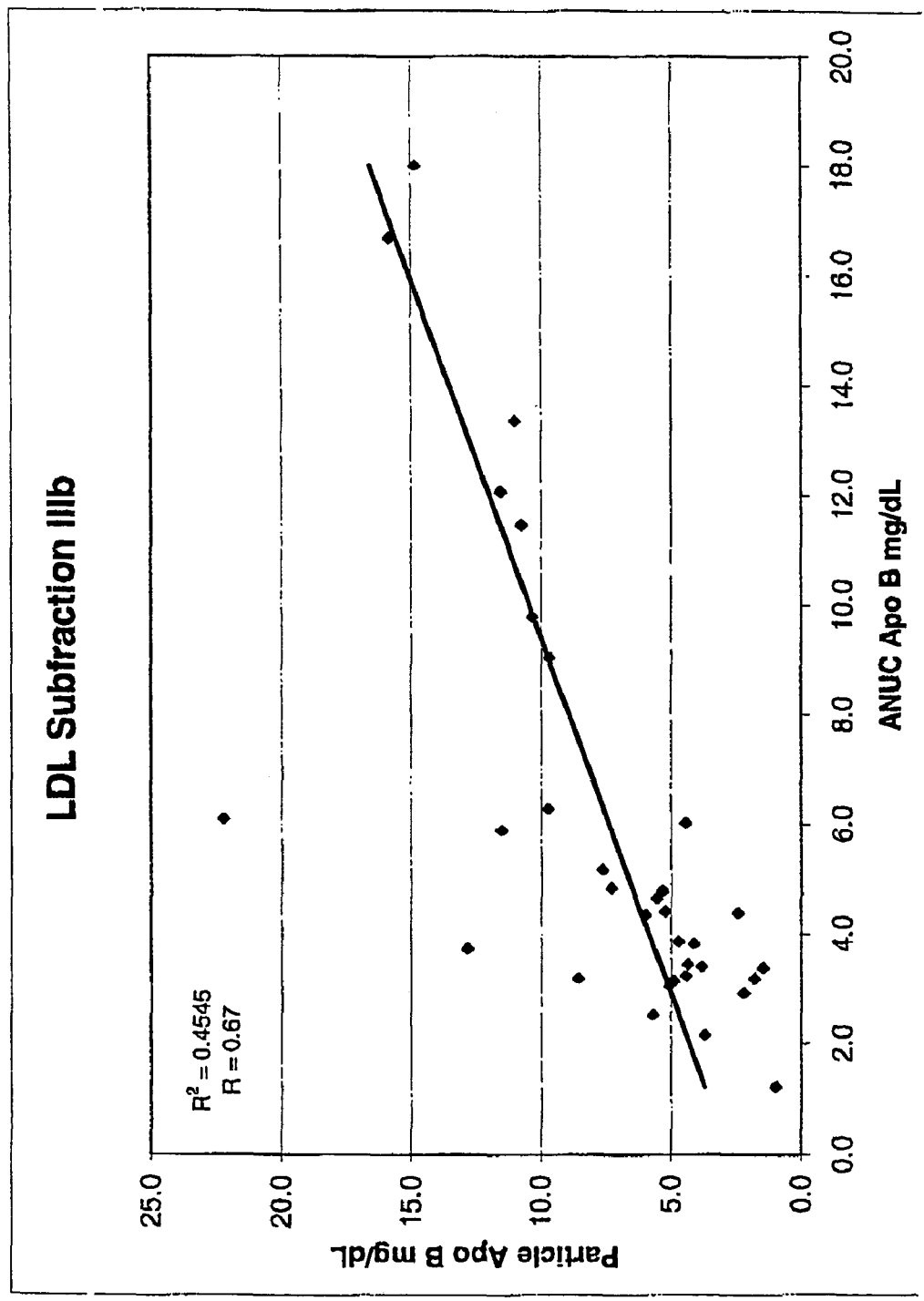
FIG. 18 shows ANUC Apo B mg/dl vs. particles ApoB mg/dl for LDL IIIb
Figure 19:
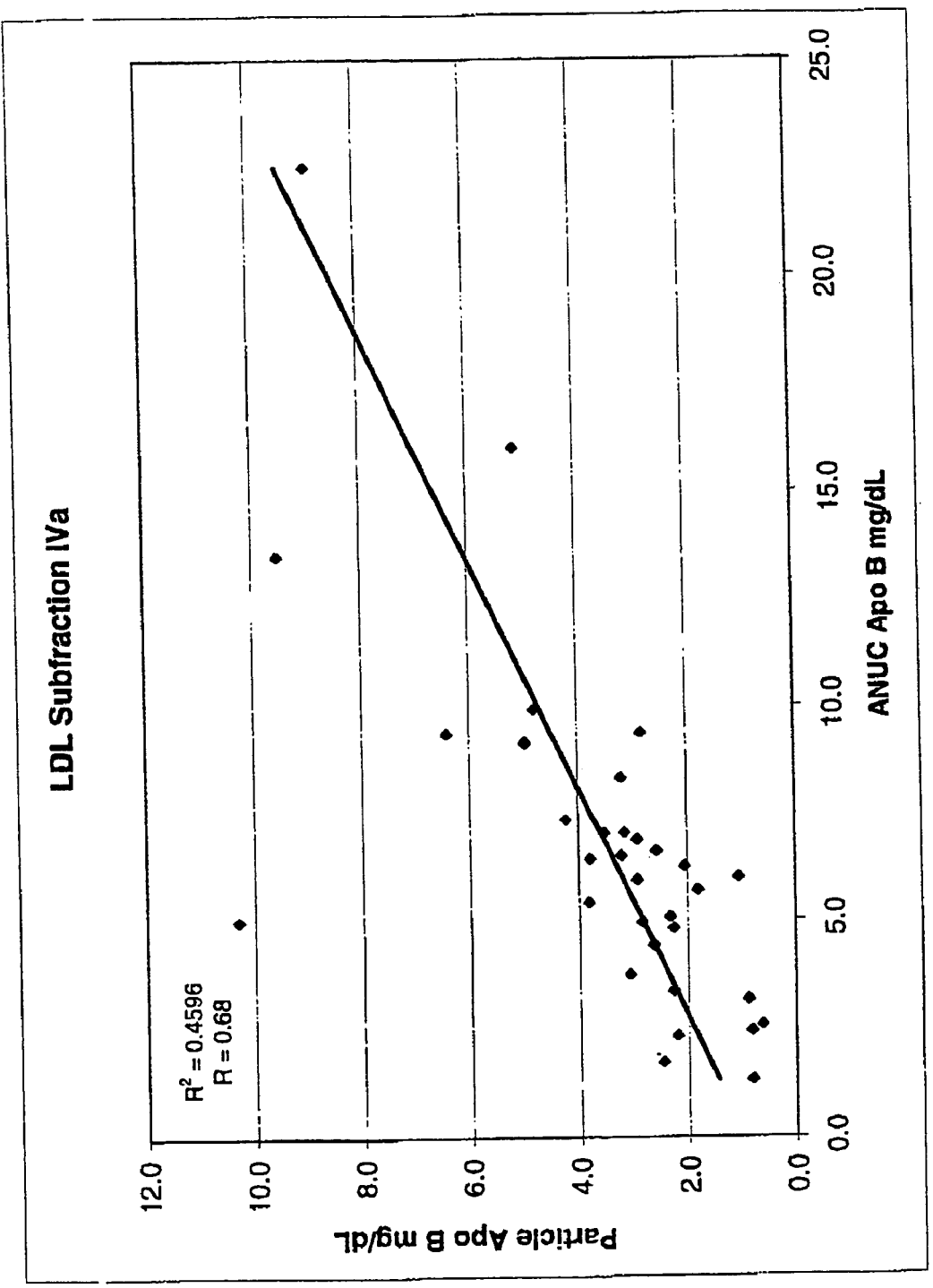
FIG. 19 shows ANUC Apo B mg/dl vs. particles ApoB mg/dl for LDL IVa
Figure 20:
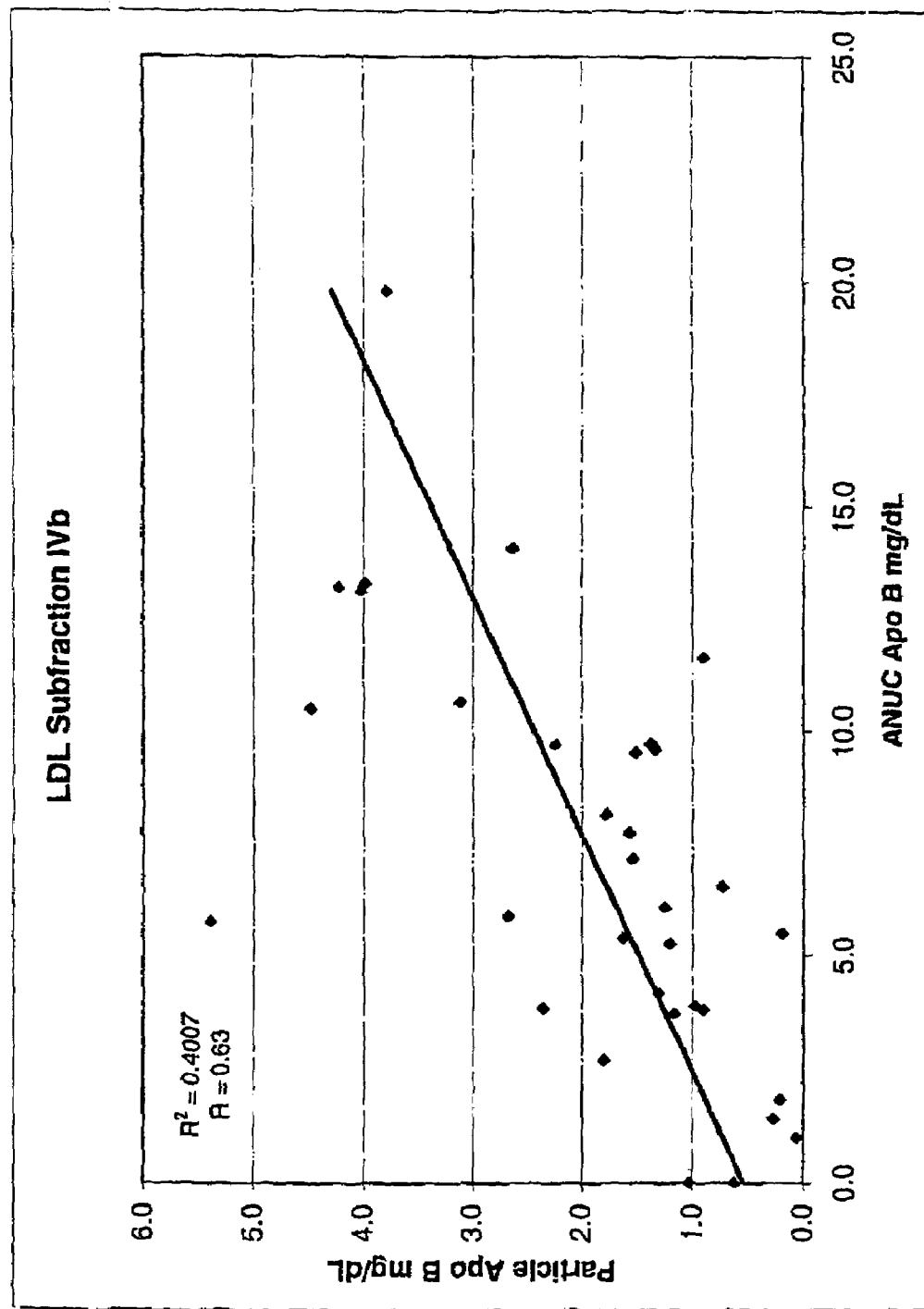
FIG. 20 shows ANUC Apo B mg/dl vs. particles ApoB mg/dl for LDL IVb
FIGS. 21(a) and 21(b) respectively show ANUC mg/dl lipoprotein vs. GGE mg/dl LDLC for LDL I and LDL IIa.
Figure 21A:
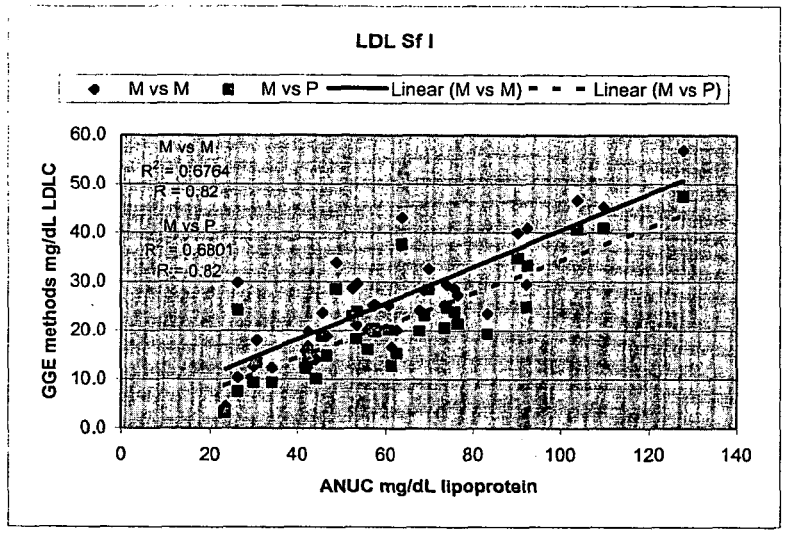
Figure 21B:
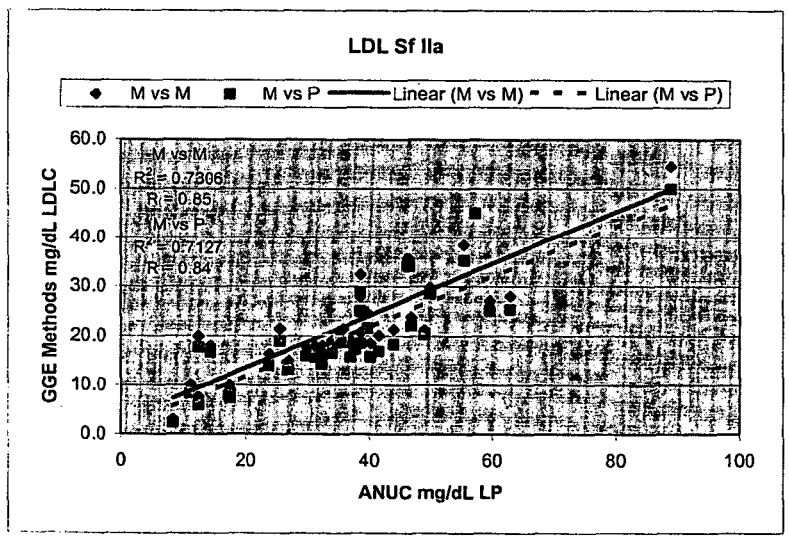
Figure 22:
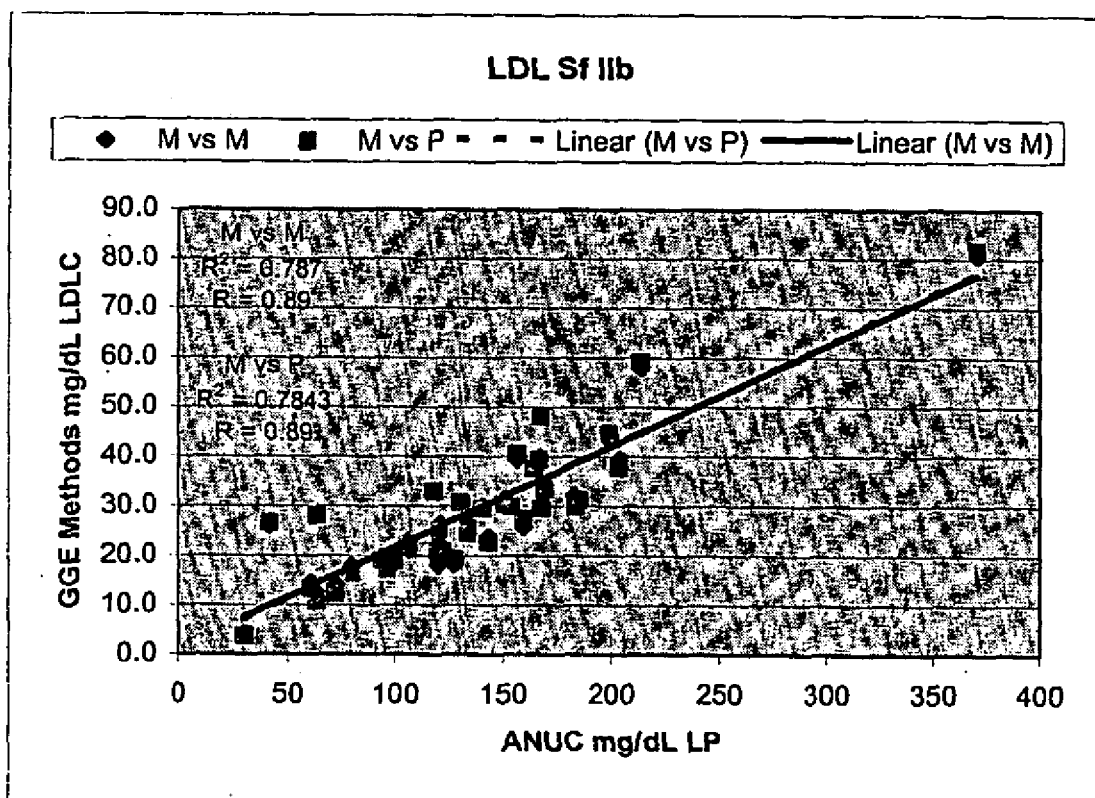
FIG. 22 show ANUC mg/dl lipoprotein vs. GGE mg/dl LDLC for LDL IIb
FIGS. 23(a) and 23(b) respectively show ANUC mg/dl lipoprotein vs. GGE mg/dl LDLC for LDL IIIa and LDL IVa
FIGS. 24(a) and 24(b) respectively show show ANUC mg/dl lipoprotein vs. GGE mg/dl LDLC for LDL IIIb and LDL IVb
Figure 23A:
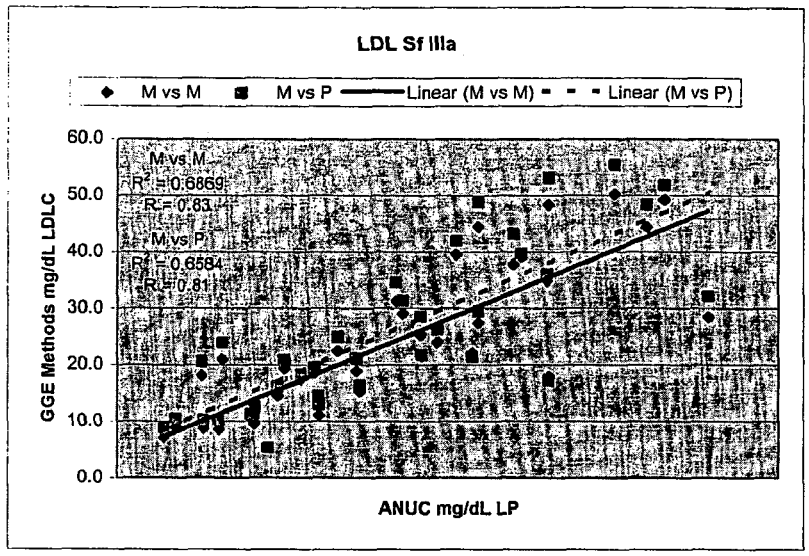
Figure 23B:
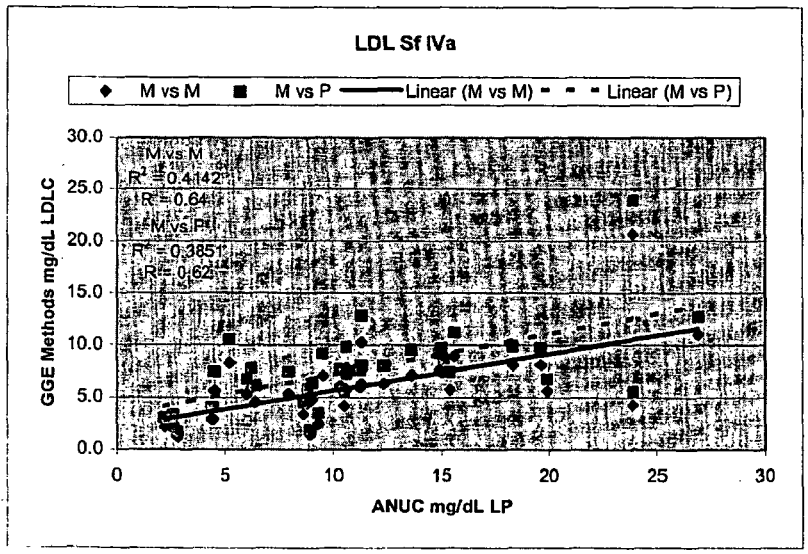
Figure 24A:
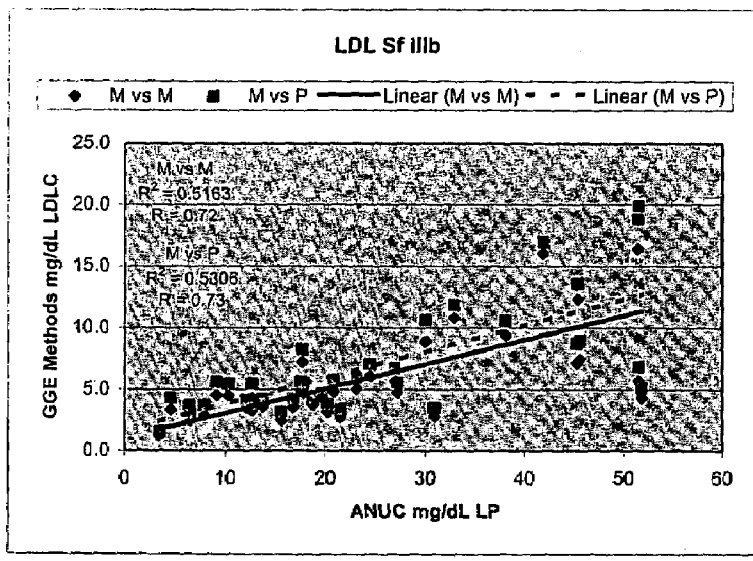
Figure 24B:
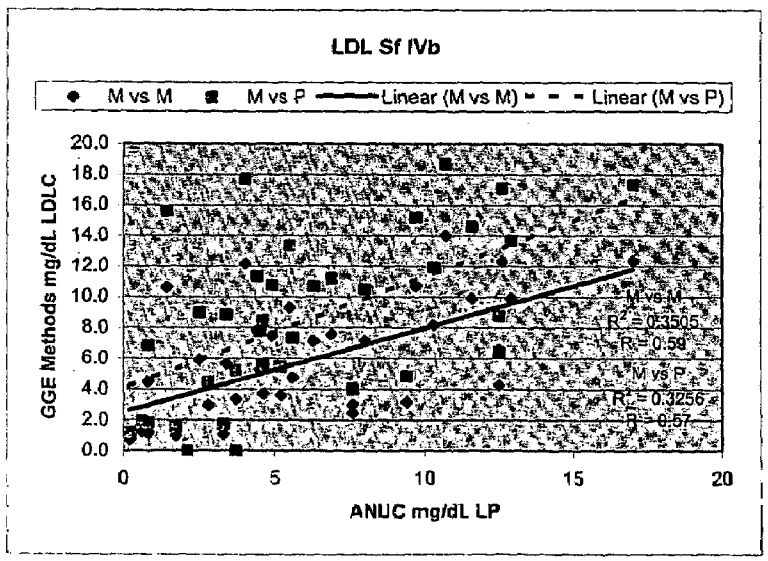

FIGS. 14 thorough 20 show correlation of ANUC ApoB mg/dl verses particle ApoB mg/dl for LDL subfractions I, Ia, IIb, IIIa, IIIb, IVa, IVb.

FIGS. 21a and 21b, 22, 23a and 23b show the correlation of ANUC mg/dl-LP to GGE method mg/dl for LDL I, Ia, IIb, IIIa, IIb, IVa and IVb.

The same results can be shown for the HDL subclasses quantitating to the Apo A value which also corresponds to particle number for HDL particles.

In this way the percentage distribution values of LDL and HDL subparticle are converted to quantitative mg/dL values. The invention includes a data base of HDL and LDL subclasses of particles and data from cardiovascular disease patient. The invention includes ratios of HDL and LDL subclasses of particles in mg/dL which corresponds to cardiovascular disease. A data base that correlate mg/dL values with a patient's data and allows for the detection and monitoring of cardiovascular disease and selection treatment for such disease.

These examples illustrate the invention and are not intended to limit it in spirit or scope.

What is claimed is:

1. A method of monitoring cardiovascular disease in a patient comprising measuring one or more LDL or HDL particle subclass levels in a biological sample from the patient and comparing the levels to a database from 65,000 cardiovascular patients, wherein the database comprises data for LDL IVb subclass in mg/Dl, HDL 2b subclass in mg/Dl, and LDL IIIa & LDL IIIb subclasses in mg/Dl, wherein the data for the LDL IVb, HDL 2b, LDL IIIa and LDL IIIb subclasses in mg/Dl are correlated to cardiovascular disease.

* * * * *